US007812126B2

(12) United States Patent
Parham et al.

(10) Patent No.: US 7,812,126 B2
(45) Date of Patent: Oct. 12, 2010

(54) DIRS1 POLYPEPTIDES

(75) Inventors: Christi L. Parham, Menlo Park, CA (US); Kevin W. Moore, Palo Alto, CA (US); Nicholas J. Murgolo, Millington, NJ (US); J. Fernando Bazan, Menlo Park, CA (US)

(73) Assignee: Schering Corporation, Kenilworth, NJ (US)

( * ) Notice: Subject to any disclaimer, the term of this patent is extended or adjusted under 35 U.S.C. 154(b) by 246 days.

(21) Appl. No.: 12/042,165

(22) Filed: Mar. 4, 2008

(65) Prior Publication Data
US 2008/0233111 A1 Sep. 25, 2008

Related U.S. Application Data

(62) Division of application No. 10/412,749, filed on Apr. 10, 2003, now Pat. No. 7,342,103, which is a division of application No. 09/265,540, filed on Mar. 8, 1999, now Pat. No. 6,586,228.

(60) Provisional application No. 60/077,329, filed on Mar. 9, 1998.

(51) Int. Cl.
C07K 14/00 (2006.01)
C07K 14/52 (2006.01)
C12N 15/00 (2006.01)
C12N 5/02 (2006.01)
C12N 5/10 (2006.01)
C12P 21/04 (2006.01)

(52) U.S. Cl. ............... 530/350; 530/351; 435/69.5; 435/69.7; 435/325; 435/361; 930/142

(58) Field of Classification Search ............... None
See application file for complete search history.

(56) References Cited

U.S. PATENT DOCUMENTS 5,350,836 A 9/1994 Kopchick et al.

FOREIGN PATENT DOCUMENTS

WO WO 95/05847 3/1995
WO WO 95/16036 6/1995

OTHER PUBLICATIONS

Bach, E., et al., (1997) *Annu. Rev. Immunol.* 15:563-591, "The IFNγ Receptor: A Paradigm for Cytokine Receptor Signaling".
Blumberg, H. et al., (2001) *Cell* 104:9-19 "Interleukin 20: Discovery, Receptor Identification, and Rold in Epidermal Function".
Gibbs V., et al., (1997) *Gene* 186(1):97-101 CRF2-4: isolation of cDNA clones encoding the human and mouse proteins.
Hemmi, S., et al., (1994) *Cell* 76(5):803-810, A Novel Member of the Interferon Receptor Family Complements Functionality of the Murine Interferon γ Receptor in Human Cells.
Hillier, L. et al., GenBank, Accession No. AA455558, Jun. 6, 1997. Definition: "aa16f06.r1 SoaresNhHMPu_S1 *Homo sapiens* cDNA clone IMAGE:813443 5', mRNA sequence".
Kotenko, S.V., et al., (1995) *J. Biol. Chem.* 270(36):20915-20921, "Interaction between the components of the Interferon γ Receptor Complex".
Kotenko, S.V., et al., (1997) *EMBO Journal* 16(19):5894-5903, "Identification and functional characterization of a second chain of the interleukin-10 receptor complex".
Liu, Y., et al., (1994) *Journal of Immunology* 152(4):1821-1829, "Expression Cloning and Characterization of a Human IL-10 Receptor".
Liu, Y., et al., (1997) *Journal of Immunology* 158(2):604-613, "The EBV IL-10 Homologue Is a Selective Agonist with Impaired Binding to the IL-10 Receptor".
Lutfalla, G., et al., (1993) *Genomics* 16(2):366-373, "A New Member of the Cytokine Receptor Gene Family Maps on Chromosome 21 at Less Than 35 kb from IFNAR".
Lutfalla, G. et al., (1996) *GenPept*, Accession No. 729209, Definition: "Cytokine Receptor Class-II CRF2-4 Precursor".
Murdoch and Finn, (2000) *Blood* 95(10):3032-3043, "Chemokine Receptors and Their Role in Inflammation and Infectious Diseases".
Pilbeam et al., (1993) *Bone* 14:717-720, "Comparison of the Effects of Various Lengths of Synthetic Human Parathyroid Hormone-Related Peptide (hPTHrP) of Malignancy on Bone Resorption and Formation in Organ Culture".
Pestka, S., (1997) *Seminars in Oncology*, 24(3), suppl. 9.:S9-18-S9-40, "The Interferon Receptors".
Soh, J., et al., (1994) *Cell* 76(5):793-802, "Identification and Sequence of an Accessory Factor Required for Activation of the Human Interferon γ Receptor".
Soh, J., et al., (1997) *GenPept* Accession No. 585319, Definition: "Interferon-Gamma Receptor Beta Chain Precursor (Interferon-Gamma Receptor Accessory Factor-1) (AF-1) (Interferon-Gamma Transducer-1)".
Spencer, S.D., et al., (1998) *J. Exp. Med.* 187(4):571-578, "The Orphan Receptor CRF2-4 Is an Essential Subunit of the Interleukin 10 Receptor".
Uzé, G., et al., (1995) *J. Interferon Cytokine Res.* 15(1):3-26, "α and β Interferons and their Friends and Relations".
Zuker, C., et al., (1984) *Proc. Natl. Acad. Sci., USA* 81:2660-2664, "*Dictyostelium* transportable element DIRS-1 has 350-base-pair inverted terminal repeats that contain a heat shock promoter".

*Primary Examiner*—Jeffrey Stucker
*Assistant Examiner*—Aditi Dutt
(74) *Attorney, Agent, or Firm*—Sheela Mohan-Peterson

(57) ABSTRACT

Nucleic acids encoding mammalian, e.g., primate or rodent receptors, purified receptor proteins and fragments thereof. Antibodies, both polyclonal and monoclonal, are also provided. Methods of using the compositions for both diagnostic and therapeutic utilities are provided.

10 Claims, No Drawings

SEQUENCE LISTING

```
<160> NUMBER OF SEQ ID NOS: 6

<210> SEQ ID NO 1
<211> LENGTH: 1381
<212> TYPE: DNA
<213> ORGANISM: Homo sapiens
<220> FEATURE:
<221> NAME/KEY: CDS
<222> LOCATION: (132)..(1064)
<220> FEATURE:
<221> NAME/KEY: misc_feature
<222> LOCATION: (567)..(567)
<223> OTHER INFORMATION: unknown nucleotide
<220> FEATURE:
<221> NAME/KEY: misc_feature
<222> LOCATION: (573)..(573)
<223> OTHER INFORMATION: unknown nucleotide
<220> FEATURE:
<221> NAME/KEY: misc_feature
<222> LOCATION: (1336)..(1336)
<223> OTHER INFORMATION: unknown nucleotide
<220> FEATURE:
<221> NAME/KEY: misc_feature
<222> LOCATION: (1342)..(1342)
<223> OTHER INFORMATION: unknown nucleotide
<220> FEATURE:
<221> NAME/KEY: misc_feature
<222> LOCATION: (1369)..(1369)
<223> OTHER INFORMATION: unknown nucleotide

<400> SEQUENCE: 1
tcgacccacg cgtccgcgct gcgactcaga cctcagctcc aacatatgca ttctgaagaa      60
agatggctga gatggacaga atgctttatt ttggaaagaa acaatgttct aggtcaaact     120
gagtctacca a atg cag act ttc aca atg gtt cta gaa gaa atc tgg aca     170
              Met Gln Thr Phe Thr Met Val Leu Glu Glu Ile Trp Thr
                1               5                  10
```

```
agt ctt ttc atg tgg ttt ttc tac gca ttg att cca tgt ttg ctc aca    218
Ser Leu Phe Met Trp Phe Phe Tyr Ala Leu Ile Pro Cys Leu Leu Thr
    15                  20                  25 gat gaa gtg gcc att ctg cct gcc cct cag aac ctc tct gta ctc tca    266
Asp Glu Val Ala Ile Leu Pro Ala Pro Gln Asn Leu Ser Val Leu Ser
30                  35                  40                  45 acc aac atg aag cat ctc ttg atg tgg agc cca gtg atc gcg cct gga    314
Thr Asn Met Lys His Leu Leu Met Trp Ser Pro Val Ile Ala Pro Gly
                50                  55                  60 gaa aca gtg tac tat tct gtc gaa tac cag ggg gag tac gag agc ctg    362
Glu Thr Val Tyr Tyr Ser Val Glu Tyr Gln Gly Glu Tyr Glu Ser Leu
            65                  70                  75 tac acg agc cac atc tgg atc ccc agc agc tgg tgc tca ctc act gaa    410
Tyr Thr Ser His Ile Trp Ile Pro Ser Ser Trp Cys Ser Leu Thr Glu
        80                  85                  90 ggt cct gag tgt gat gtc act gat gac atc acg gcc act gtg cca tac    458
Gly Pro Glu Cys Asp Val Thr Asp Asp Ile Thr Ala Thr Val Pro Tyr
    95                  100                 105 aac ctt cgt gtc agg gcc aca ttg ggc tca cag acc tca gcc tgg agc    506
Asn Leu Arg Val Arg Ala Thr Leu Gly Ser Gln Thr Ser Ala Trp Ser
110                 115                 120                 125 atc ctg aag cat ccc ttt aat aga aac tca acc atc ctt acc cga cct    554
Ile Leu Lys His Pro Phe Asn Arg Asn Ser Thr Ile Leu Thr Arg Pro
                130                 135                 140 ggg atg gag atc ncc aaa nat ggc ttc cac ctg gtt att gag ctg gag    602
Gly Met Glu Ile Xaa Lys Xaa Gly Phe His Leu Val Ile Glu Leu Glu
            145                 150                 155 gac ctg ggg ccc cag ttt gag ttc ctt gtg gcc tac tgg asg agg gag    650
Asp Leu Gly Pro Gln Phe Glu Phe Leu Val Ala Tyr Trp Xaa Arg Glu
        160                 165                 170 cct ggt gcc gag gaa cat gtc aaa atg gtg agg agt ggg ggt att cca    698
Pro Gly Ala Glu Glu His Val Lys Met Val Arg Ser Gly Gly Ile Pro
    175                 180                 185 gtg cac cta gaa acc atg gag cca ggg gct gca tac tgt gtg aag gcc    746
Val His Leu Glu Thr Met Glu Pro Gly Ala Ala Tyr Cys Val Lys Ala
190                 195                 200                 205 cag aca ttc gtg aag gcc att ggg arg tac agc gcc ttc agc cag aca    794
Gln Thr Phe Val Lys Ala Ile Gly Xaa Tyr Ser Ala Phe Ser Gln Thr
                210                 215                 220 gaa tgt gtg gar gtg caa gga gag gcc att ccc ctg gta ctg gcc ctg    842
Glu Cys Val Glu Val Gln Gly Glu Ala Ile Pro Leu Val Leu Ala Leu
            225                 230                 235 ttt gcc ttt gtt ggc ttc atg ctg atc ctt gtg gtc gtg cca ctg ttc    890
Phe Ala Phe Val Gly Phe Met Leu Ile Leu Val Val Val Pro Leu Phe
        240                 245                 250 gtc tgg aaa atg ggc cgg ctc ctc cag tac tcc tgt tgc ccc gtg gtg    938
Val Trp Lys Met Gly Arg Leu Leu Gln Tyr Ser Cys Cys Pro Val Val
    255                 260                 265 gtc ctc cca gac acc ttg aaa ata acc aat tca ccc cag aag tta atc    986
Val Leu Pro Asp Thr Leu Lys Ile Thr Asn Ser Pro Gln Lys Leu Ile
270                 275                 280                 285 agc tgc aga agg gag gag gtg gat gcc tgt gcc acg gct gtg atg tct    1034
Ser Cys Arg Arg Glu Glu Val Asp Ala Cys Ala Thr Ala Val Met Ser
                290                 295                 300 cct gag gaa ctc ctc agg gcc tgg atc tca taggtttgcg gaagggccca     1084
Pro Glu Glu Leu Leu Arg Ala Trp Ile Ser
            305                 310 ggtgaagccg agaacctggt ctgcatgaca tggaaaccat gaggggacaa gttgtgtttc    1144
```

```
tgttttccgc cacggacaag ggatgagaga agtaggaaga gcctgttgtc tacaagtcta   1204
gaagcaacca tcagaggcag ggtggtttgt ckaacagaac aaytgactga ggytakrggg   1264
gwtgtgacct ctagactktg ggstkscayt tgcwtggytg agcaaccctg ggaaaagtga   1324
cttcatccct tnggtccnaa gttttctcat ctgtaatggg ggatncctac aaaactg     1381
```

<210> SEQ ID NO 2
<211> LENGTH: 311
<212> TYPE: PRT
<213> ORGANISM: Homo sapiens
<220> FEATURE:
<221> NAME/KEY: misc_feature
<222> LOCATION: (146)..(146)
<223> OTHER INFORMATION: The 'Xaa' at location 146 stands for Thr, Ala,
      Pro, or Ser.
<220> FEATURE:
<221> NAME/KEY: misc_feature
<222> LOCATION: (148)..(148)
<223> OTHER INFORMATION: The 'Xaa' at location 148 stands for Asn, Asp,
      His, or Tyr.
<220> FEATURE:
<221> NAME/KEY: misc_feature
<222> LOCATION: (171)..(171)
<223> OTHER INFORMATION: The 'Xaa' at location 171 stands for Arg, or
      Thr.
<220> FEATURE:
<221> NAME/KEY: misc_feature
<222> LOCATION: (214)..(214)
<223> OTHER INFORMATION: The 'Xaa' at location 214 stands for Arg, or
      Lys.

<400> SEQUENCE: 2

Met Gln Thr Phe Thr Met Val Leu Glu Glu Ile Trp Thr Ser Leu Phe
1               5                   10                  15

Met Trp Phe Phe Tyr Ala Leu Ile Pro Cys Leu Leu Thr Asp Glu Val
            20                  25                  30

Ala Ile Leu Pro Ala Pro Gln Asn Leu Ser Val Leu Ser Thr Asn Met
        35                  40                  45

Lys His Leu Leu Met Trp Ser Pro Val Ile Ala Pro Gly Glu Thr Val
    50                  55                  60

Tyr Tyr Ser Val Glu Tyr Gln Gly Glu Tyr Ser Leu Tyr Thr Ser
65                  70                  75                  80

His Ile Trp Ile Pro Ser Ser Trp Cys Ser Leu Thr Glu Gly Pro Glu
                85                  90                  95

Cys Asp Val Thr Asp Asp Ile Thr Ala Thr Val Pro Tyr Asn Leu Arg
            100                 105                 110

Val Arg Ala Thr Leu Gly Ser Gln Thr Ser Ala Trp Ser Ile Leu Lys
        115                 120                 125

His Pro Phe Asn Arg Asn Ser Thr Ile Leu Thr Arg Pro Gly Met Glu
    130                 135                 140

Ile Xaa Lys Xaa Gly Phe His Leu Val Ile Glu Leu Glu Asp Leu Gly
145                 150                 155                 160

Pro Gln Phe Glu Phe Leu Val Ala Tyr Trp Xaa Arg Glu Pro Gly Ala
                165                 170                 175

Glu Glu His Val Lys Met Val Arg Ser Gly Gly Ile Pro Val His Leu
            180                 185                 190

Glu Thr Met Glu Pro Gly Ala Ala Tyr Cys Val Lys Ala Gln Thr Phe
        195                 200                 205

Val Lys Ala Ile Gly Xaa Tyr Ser Ala Phe Ser Gln Thr Glu Cys Val
    210                 215                 220

Glu Val Gln Gly Glu Ala Ile Pro Leu Val Leu Ala Leu Phe Ala Phe

```
           225                 230                 235                 240
Val Gly Phe Met Leu Ile Leu Val Val Pro Leu Phe Val Trp Lys
                    245                 250                 255

Met Gly Arg Leu Leu Gln Tyr Ser Cys Cys Pro Val Val Leu Pro
            260                 265                 270

Asp Thr Leu Lys Ile Thr Asn Ser Pro Gln Lys Leu Ile Ser Cys Arg
        275                 280                 285

Arg Glu Glu Val Asp Ala Cys Ala Thr Ala Val Met Ser Pro Glu Glu
    290                 295                 300

Leu Leu Arg Ala Trp Ile Ser
305                 310

<210> SEQ ID NO 3
<211> LENGTH: 1244
<212> TYPE: DNA
<213> ORGANISM: Homo sapiens
<220> FEATURE:
<221> NAME/KEY: CDS
<222> LOCATION: (2)..(694)

<400> SEQUENCE: 3 c cgg gtc gac cca cgc gtc cgc ctg gtt tcc ccc tgg ctg aca gtg cct       49
  Arg Val Asp Pro Arg Val Arg Leu Val Ser Pro Trp Leu Thr Val Pro
  1               5                   10                  15 tgg ttc ctg tcc tgt tgg aat gtt acc att ggg cct cct gag agc atc        97
Trp Phe Leu Ser Cys Trp Asn Val Thr Ile Gly Pro Pro Glu Ser Ile
            20                  25                  30 tgg gtg acg ccg gga gaa gcc tcc ctc atc atc agg ttc tcc tct ccc       145
Trp Val Thr Pro Gly Glu Ala Ser Leu Ile Ile Arg Phe Ser Ser Pro
        35                  40                  45 ttc gac gtc cct ccc aac ctg ggc tat ttc cag tac tat gtc cat tay       193
Phe Asp Val Pro Pro Asn Leu Gly Tyr Phe Gln Tyr Tyr Val His Tyr
    50                  55                  60 tgg gaa aag gcg gga atc caa aag gtt aaa ggt cct ttc aag agc aac       241
Trp Glu Lys Ala Gly Ile Gln Lys Val Lys Gly Pro Phe Lys Ser Asn
65                  70                  75                  80 tcc atc gtg ttg gat ggc ttg aga ccc tta aga gaa tac tgt tta caa       289
Ser Ile Val Leu Asp Gly Leu Arg Pro Leu Arg Glu Tyr Cys Leu Gln
                85                  90                  95 gtg aag gcg cat ctc ttt cgc aca tcc tgc aac acc tct agg ccc ggc       337
Val Lys Ala His Leu Phe Arg Thr Ser Cys Asn Thr Ser Arg Pro Gly
            100                 105                 110 cgc tta agc aac ata act tgc tac gaa aca atg atg gat gcc act acg       385
Arg Leu Ser Asn Ile Thr Cys Tyr Glu Thr Met Met Asp Ala Thr Thr
        115                 120                 125 aag ctt caa caa gtc atc ctc atc gcc gtg gga gtc ttt ctg tcg ctg       433
Lys Leu Gln Gln Val Ile Leu Ile Ala Val Gly Val Phe Leu Ser Leu
    130                 135                 140 gcg gcg ctg gcg ggg ggc tgt ttc ttc ctg gtg ctg aga tac aaa ggc       481
Ala Ala Leu Ala Gly Gly Cys Phe Phe Leu Val Leu Arg Tyr Lys Gly
145                 150                 155                 160 ctg gtg aaa tac tgg ttt cac tct ccg cca agc atc cca tca caa atc       529
Leu Val Lys Tyr Trp Phe His Ser Pro Pro Ser Ile Pro Ser Gln Ile
                165                 170                 175 gaa gag tat ctg aag gac ccg agc cag cct atc cta gag gcc ctg gac       577
Glu Glu Tyr Leu Lys Asp Pro Ser Gln Pro Ile Leu Glu Ala Leu Asp
            180                 185                 190 aag gac acg tca cca aca gat gat gcc tgg gac ttg gtg tct gtt gtt       625
Lys Asp Thr Ser Pro Thr Asp Asp Ala Trp Asp Leu Val Ser Val Val
        195                 200                 205
```

```
gca ttt cca gca aag gag caa gaa gat gtt ccc caa agc act ttg acc     673
Ala Phe Pro Ala Lys Glu Gln Glu Asp Val Pro Gln Ser Thr Leu Thr
    210                 215                 220 caa aac tct ggt gcg gtc tgc tagcctgtgg ggtaagggct ctgagccgag        724
Gln Asn Ser Gly Ala Val Cys
225                 230 gaagctgctg atgtccatgt cagcacttta tggaatccgg tcctccattt tcctgtcccc   784
aaaaggcccg tcagtgcctg tgaagatgta acgggtctca tggggcgac aagcttattg    844 atttttttct tcaaactaag agttttctaa tcatacgcgt ttttagaata attctacaga   904
tatgtccccg aaagattaag atttctctta aacactaaaa agacatgtaa ttatttgtta   964
gcaaatgggc gtctggcacg cctctgacac ttttcgtca gcagccagga cacgaggtcc   1024
cctccttgat gaagcccctc gggcagacca tgtcacctgt cccagcctgc cccaagaagg  1084
gacattaagt ggcccttctt catatccaaa cacctggctt gaatgtgat tagccctgta   1144 aatagtttca cagagattaa gccttttttt cccccaagtt aggaataaaa gactataatt  1204
aactttttaa aaaaaaaaaa aaaaaaaaaa aaaaaaaaa                         1244
```

<210> SEQ ID NO 4
<211> LENGTH: 231
<212> TYPE: PRT
<213> ORGANISM: Homo sapiens

<400> SEQUENCE: 4

```
Arg Val Asp Pro Arg Val Arg Leu Val Ser Pro Trp Leu Thr Val Pro
1               5                   10                  15

Trp Phe Leu Ser Cys Trp Asn Val Thr Ile Gly Pro Pro Glu Ser Ile
            20                  25                  30

Trp Val Thr Pro Gly Glu Ala Ser Leu Ile Ile Arg Phe Ser Ser Pro
        35                  40                  45

Phe Asp Val Pro Pro Asn Leu Gly Tyr Phe Gln Tyr Tyr Val His Tyr
    50                  55                  60

Trp Glu Lys Ala Gly Ile Gln Lys Val Lys Gly Pro Phe Lys Ser Asn
65                  70                  75                  80

Ser Ile Val Leu Asp Gly Leu Arg Pro Leu Arg Glu Tyr Cys Leu Gln
                85                  90                  95

Val Lys Ala His Leu Phe Arg Thr Ser Cys Asn Thr Ser Arg Pro Gly
            100                 105                 110

Arg Leu Ser Asn Ile Thr Cys Tyr Glu Thr Met Met Asp Ala Thr Thr
        115                 120                 125

Lys Leu Gln Gln Val Ile Leu Ile Ala Val Gly Val Phe Leu Ser Leu
    130                 135                 140

Ala Ala Leu Ala Gly Gly Cys Phe Phe Leu Val Leu Arg Tyr Lys Gly
145                 150                 155                 160

Leu Val Lys Tyr Trp Phe His Ser Pro Ser Ile Pro Ser Gln Ile
                165                 170                 175

Glu Glu Tyr Leu Lys Asp Pro Ser Gln Pro Ile Leu Glu Ala Leu Asp
            180                 185                 190

Lys Asp Thr Ser Pro Thr Asp Asp Ala Trp Asp Leu Val Ser Val Val
        195                 200                 205

Ala Phe Pro Ala Lys Glu Gln Glu Asp Val Pro Gln Ser Thr Leu Thr
    210                 215                 220

Gln Asn Ser Gly Ala Val Cys
225                 230
```

<210> SEQ ID NO 5
<211> LENGTH: 337
<212> TYPE: PRT
<213> ORGANISM: Homo sapiens

<400> SEQUENCE: 5

Met Arg Pro Thr Leu Leu Trp Ser Leu Leu Leu Leu Gly Val Phe
1               5                   10                  15

Ala Ala Ala Ala Ala Pro Pro Asp Pro Leu Ser Gln Leu Pro Ala
            20                  25                  30

Pro Gln His Pro Lys Ile Arg Leu Tyr Asn Ala Glu Gln Val Leu Ser
        35                  40                  45

Trp Glu Pro Val Ala Leu Ser Asn Ser Thr Arg Pro Val Val Tyr Arg
    50                  55                  60

Val Gln Phe Lys Tyr Thr Asp Ser Lys Trp Phe Thr Ala Asp Ile Met
65                  70                  75                  80

Ser Ile Gly Val Asn Cys Thr Gln Ile Thr Ala Thr Glu Cys Asp Phe
                85                  90                  95

Thr Ala Ala Ser Pro Ser Ala Gly Phe Pro Met Asp Phe Asn Val Thr
            100                 105                 110

Leu Arg Leu Arg Ala Glu Leu Gly Ala Leu His Ser Ala Trp Val Thr
        115                 120                 125

Met Pro Trp Phe Gln His Tyr Arg Asn Val Thr Val Gly Pro Pro Glu
    130                 135                 140

Asn Ile Glu Val Thr Pro Gly Glu Gly Ser Leu Ile Ile Arg Phe Ser
145                 150                 155                 160

Ser Pro Phe Asp Ile Ala Asp Thr Ser Thr Ala Phe Phe Cys Tyr Tyr
                165                 170                 175

Val His Tyr Trp Glu Lys Gly Gly Ile Gln Gln Val Lys Gly Pro Phe
            180                 185                 190

Arg Ser Asn Ser Ile Ser Leu Asp Asn Leu Lys Pro Ser Arg Val Tyr
        195                 200                 205

Cys Leu Gln Val Gln Ala Gln Leu Leu Trp Asn Lys Ser Asn Ile Phe
210                 215                 220

Arg Val Gly His Leu Ser Asn Ile Ser Cys Tyr Glu Thr Met Ala Asp
225                 230                 235                 240

Ala Ser Thr Glu Leu Gln Gln Val Ile Leu Ile Ser Val Gly Thr Phe
                245                 250                 255

Ser Leu Leu Ser Val Leu Ala Gly Ala Cys Phe Phe Leu Val Leu Lys
            260                 265                 270

Tyr Arg Gly Leu Ile Lys Tyr Trp Phe His Thr Pro Pro Ser Ile Pro
        275                 280                 285

Leu Gln Ile Glu Glu Tyr Leu Lys Asp Pro Thr Gln Pro Ile Leu Glu
    290                 295                 300

Ala Leu Asp Lys Asp Ser Ser Pro Lys Asp Asp Val Trp Asp Ser Val
305                 310                 315                 320

Ser Ile Ile Ser Phe Pro Glu Lys Glu Gln Glu Asp Val Leu Gln Thr
                325                 330                 335

Leu

<210> SEQ ID NO 6
<211> LENGTH: 325
<212> TYPE: PRT
<213> ORGANISM: Homo sapiens

```
<400> SEQUENCE: 6

Met Ala Trp Ser Leu Gly Ser Trp Leu Gly Cys Leu Leu Val Ser
1               5                   10                  15

Ala Leu Gly Met Val Pro Pro Glu Asn Val Arg Met Asn Ser Val
            20                  25                  30

Asn Phe Lys Asn Ile Leu Gln Trp Glu Ser Pro Ala Phe Ala Lys Gly
        35                  40                  45

Asn Leu Thr Phe Thr Ala Gln Tyr Leu Ser Tyr Arg Ile Phe Gln Asp
        50                  55                  60

Lys Cys Met Asn Thr Thr Leu Thr Glu Cys Asp Phe Ser Ser Leu Ser
65                  70                  75                  80

Lys Tyr Gly Asp His Thr Leu Arg Val Arg Ala Glu Phe Ala Asp Glu
                85                  90                  95

His Ser Asp Trp Val Asn Ile Thr Phe Cys Pro Val Asp Asp Thr Ile
            100                 105                 110

Ile Gly Pro Pro Gly Met Gln Val Glu Val Leu Ala Asp Ser Leu His
        115                 120                 125

Met Arg Phe Leu Ala Pro Lys Ile Glu Asn Glu Tyr Glu Thr Trp Thr
    130                 135                 140

Met Lys Asn Val Tyr Asn Ser Trp Thr Tyr Asn Val Gln Tyr Trp Lys
145                 150                 155                 160

Asn Gly Thr Asp Glu Lys Phe Gln Ile Thr Pro Gln Tyr Asp Phe Glu
            165                 170                 175

Val Leu Arg Asn Leu Glu Pro Trp Thr Thr Tyr Cys Val Gln Val Arg
        180                 185                 190

Gly Phe Leu Pro Asp Arg Asn Lys Ala Gly Glu Trp Ser Glu Pro Val
    195                 200                 205

Cys Glu Gln Thr Thr His Asp Glu Thr Val Pro Ser Trp Met Val Ala
    210                 215                 220

Val Ile Leu Met Ala Ser Val Phe Met Val Cys Leu Ala Leu Leu Gly
225                 230                 235                 240

Cys Phe Ser Leu Leu Trp Cys Val Tyr Lys Lys Thr Lys Tyr Ala Phe
            245                 250                 255

Ser Pro Arg Asn Ser Leu Pro Gln His Leu Lys Glu Phe Leu Gly His
        260                 265                 270

Pro His His Asn Thr Leu Leu Phe Phe Ser Phe Pro Leu Ser Asp Glu
    275                 280                 285

Asn Asp Val Phe Asp Lys Leu Ser Val Ile Ala Glu Asp Ser Glu Ser
    290                 295                 300

Gly Lys Gln Asn Pro Gly Asp Ser Cys Ser Leu Gly Thr Pro Pro Gly
305                 310                 315                 320

Gln Gly Pro Gln Ser
                325
```

DIRS1 POLYPEPTIDES

This filing is a divisional of U.S. patent application Ser. No. 10/412,749, filed Apr. 10, 2003, U.S. Pat. No. 7,342,103, which is a divisional of U.S. patent application Ser. No. 09/265,540, filed Mar. 8, 1999, U.S. Pat. No. 6,586,228, which claims benefit from U.S. Provisional Patent Application No. 60/077,329, filed Mar. 9, 1998, each of which is incorporated herein by reference.

FIELD OF THE INVENTION

The present invention relates to compositions and methods for affecting mammalian physiology, including morphogenesis or immune system function. In particular, it provides nucleic acids, proteins, and antibodies which regulate development and/or the immune system. Diagnostic and therapeutic uses of these materials are also disclosed.

BACKGROUND OF THE INVENTION

Recombinant DNA technology refers generally to techniques of integrating genetic information from a donor source into vectors for subsequent processing, such as through introduction into a host, whereby the transferred genetic information is copied and/or expressed in the new environment. Commonly, the genetic information exists in the form of complementary DNA (cDNA) derived from messenger RNA (mRNA) coding for a desired protein product. The carrier is frequently a plasmid having the capacity to incorporate cDNA for later replication in a host and, in some cases, actually to control expression of the cDNA and thereby direct synthesis of the encoded product in the host. See, e.g., Sambrook, et al. (1989) *Molecular Cloning: A Laboratory Manual*, (2d ed.), vols. 1-3, CSH Press, NY.

For some time, it has been known that the mammalian immune response is based on a series of complex cellular interactions, called the "immune network". Recent research has provided new insights into the inner workings of this network. While it remains clear that much of the immune response does, in fact, revolve around the network-like interactions of lymphocytes, macrophages, granulocytes, and other cells, immunologists now generally hold the opinion that soluble proteins, known as lymphokines, cytokines, or monokines, play critical roles in controlling these cellular interactions. The interferons are generally considered to be members of the cytokine family. Thus, there is considerable interest in the isolation, characterization, and mechanisms of action of cell modulatory factors, an understanding of which will lead to significant advancements in the diagnosis and therapy of numerous medical abnormalities, e.g., immune system disorders.

Lymphokines apparently mediate cellular activities in a variety of ways. See, e.g., Paul (ed. 1996) *Fundamental Immunology* 3d ed., Raven Press, New York; and Thomson (ed. 1994) *The Cytokine Handbook* 2d ed., Academic Press, San Diego. They have been shown to support the proliferation, growth, and/or differentiation of pluripotential hematopoietic stem cells into vast numbers of progenitors comprising diverse cellular lineages which make up a complex immune system. Proper and balanced interactions between the cellular components are necessary for a healthy immune response. The different cellular lineages often respond in a different manner when lymphokines are administered in conjunction with other agents.

Cell lineages especially important to the immune response include two classes of lymphocytes: B-cells, which can produce and secrete immunoglobulins (proteins with the capability of recognizing and binding to foreign matter to effect its removal), and T-cells of various subsets that secrete lymphokines and induce or suppress the B-cells and various other cells (including other T-cells) making up the immune network. These lymphocytes interact with many other cell types.

One means to modulate the effect of a cytokine upon binding to its receptor, and therefore potentially useful in treating inappropriate immune responses, e.g., autoimmune, inflammation, sepsis, and cancer situations, is to inhibit the receptor signal transduction. Unfortunately, finding reagents capable of serving as an antagonist or agonist has been severely hampered by the failure to fully identify all of the components within the signaling systems. In order to characterize the structural properties of a cytokine receptor in greater detail and to understand the mechanism of action at the molecular level, purified receptor will be very useful. The receptors provided herein, by comparison to other receptors or by combining structural components, will provide further understanding of signal transduction induced by ligand binding.

The isolated receptor gene should provide means to generate an economical source of the receptor, allow expression of more receptors on a cell leading to increased assay sensitivity, promote characterization of various receptor subtypes and variants, and allow correlation of activity with receptor structures. Moreover, fragments of the receptor may be useful as agonists or antagonists of ligand binding. See, e.g., Harada, et al. (1992) *J. Biol. Chem.* 267:22752-22758. Often, there are at least two critical subunits in the functional receptor. See, e.g., Gonda and D'Andrea (1997) *Blood* 89:355-369; Presky, et al. (1996) *Proc. Nat'l Acad. Sci. USA* 93:14002-14007; Drachman and Kaushansky (1995) *Curr. Opin. Hematol.* 2:22-28; Theze (1994) *Eur. Cytokine Netw.* 5:353-368; and Lemmon and Schlessinger (1994) *Trends Biochem. Sci.* 19:459-463.

From the foregoing, it is evident that the discovery and development of new soluble proteins and their receptors, including ones similar to lymphokines, should contribute to new therapies for a wide range of degenerative or abnormal conditions which directly or indirectly involve development, differentiation, or function, e.g., of the immune system and/or hematopoietic cells. In particular, the discovery and understanding of novel receptors for lymphokine-like molecules which enhance or potentiate the beneficial activities of other lymphokines would be highly advantageous. The present invention provides new receptors for ligands exhibiting similarity to cytokine like compositions and related compounds, and methods for their use.

SUMMARY OF THE INVENTION

The present invention is directed to novel receptors related to cytokine receptors, e.g., primate or rodent, cytokine receptor like molecular structures, designated DNAX Interferon-like Receptor Subunits (DIRS), and their biological activities. In particular, it provides description of two different subunits, designated DIRS1 and DIRS2. It includes nucleic acids coding for the polypeptides themselves and methods for their production and use. The nucleic acids of the invention are characterized, in part, by their homology to cloned complementary DNA (cDNA) sequences enclosed herein.

The present invention provides, in polypeptide embodiments: a substantially pure or recombinant DIRS1 polypeptide comprising at least three distinct nonoverlapping segments of at least four amino acids identical to segments of SEQ ID NO: 2; a substantially pure or recombinant DIRS1 polypeptide comprising at least two distinct nonoverlapping segments of at least five amino acids identical to segments of SEQ ID NO: 2; a natural sequence DIRS1 comprising mature SEQ ID NO: 2; a fusion polypeptide comprising DIRS1 sequence; a substantially pure or recombinant DIRS2 polypeptide comprising at least three distinct nonoverlapping segments of at least ten amino acids identical to segments of SEQ ID NO: 4; a substantially pure or recombinant DIRS2 polypeptide comprising at least two distinct nonoverlapping segments of at least eleven amino acids identical to segments of SEQ ID NO: 4; a natural sequence DIRS2 comprising SEQ ID NO: 4; or a fusion polypeptide comprising DIRS2 sequence. Preferred embodiments include, e.g., the substantially pure or isolated antigenic: DIRS1 polypeptide, wherein the distinct nonoverlapping segments of identity: include one of at least eight amino acids; include one of at least four amino acids and a second of at least five amino acids; include at least three segments of at least four, five, and six amino acids, or include one of at least twelve amino acids; or DIRS2 polypeptide, wherein the distinct nonoverlapping segments of identity: include one of at least thirteen amino acids; include one of at least eleven amino acids and a second of at least thirteen amino acids; include at least three segments of at least ten, eleven, and twelve amino acids; or include one of at least twenty-five amino acids. Other embodiments include compositions where: the DIRS1 polypeptide: comprises a mature sequence of Table 1; is an unglycosylated form of DIRS1; is from a primate, such as a human; comprises at least seventeen amino acids of SEQ ID NO: 2; exhibits at least four nonoverlapping segments of at least seven amino acids of SEQ ID NO: 2; is a natural allelic variant of DIRS1; has a length at least about 30 amino acids; exhibits at least two nonoverlapping epitopes which are specific for a primate DIRS1; is glycosylated; has a molecular weight of at least 30 kD with natural glycosylation; is a synthetic polypeptide; is attached to a solid substrate; is conjugated to another chemical moiety; is a 5-fold or less substitution from natural sequence; or is a deletion or insertion variant from a natural sequence; or the DIRS2 polypeptide: comprises a mature sequence of Table 2; is an unglycosylated form of DIRS2; or is from a primate, such as a human; comprises at thirty-five amino acids of SEQ ID NO: 4; exhibits at least four nonoverlapping segments of at least twelve amino acids of SEQ ID NO: 4; is a natural allelic variant of DIRS2; has a length at least about 30 amino acids; exhibits at least two non-overlapping epitopes which are specific for a primate DIRS2; is glycosylated; has a molecular weight of at least 30 kD with natural glycosylation; is a synthetic polypeptide; is attached to a solid substrate; is conjugated to another chemical moiety; is a 5-fold or less substitution from natural sequence; or is a deletion or insertion variant from a natural sequence. Various combination compositions include those comprising: a substantially pure DIRS1 and another Interferon Receptor family member; a substantially pure DIRS2 and another Interferon Receptor family member; a sterile DIRS1 polypeptide; a sterile DIRS2 polypeptide; the DIRS1 polypeptide and a carrier, wherein the carrier is: an aqueous compound, including water, saline, and/or buffer; and/or formulated for oral, rectal, nasal, topical, or parenteral administration; or the DIRS2 polypeptide and a carrier, wherein the carrier is: an aqueous compound, including water, saline, and/or buffer; and/or formulated for oral, rectal, nasal, topical, or parenteral administration.

Fusion polypeptide embodiments include those comprising: mature protein sequence of Table 1; mature protein sequence of Table 2; a detection or purification tag, including a FLAG, His6, or Ig sequence; or sequence of another interferon receptor protein. Kit embodiments are provided, e.g., a kit comprising such a polypeptide, and: a compartment comprising the protein or polypeptide; or instructions for use or disposal of reagents in the kit.

The invention also provides a binding compound comprising an antigen binding site from an antibody, which specifically binds to a: natural DIRS1 polypeptide, wherein: the binding compound is in a container; the DIRS1 polypeptide is from a human; the binding compound is an Fv, Fab, or Fab2 fragment; the binding compound is conjugated to another chemical moiety; or the antibody: is raised against a peptide sequence of a mature polypeptide of Table 1; is raised against a mature DIRS1; is raised to a purified human DIRS1; is immunoselected; is a polyclonal antibody; binds to a denatured DIRS1; exhibits a Kd to antigen of at least 30 µM; is attached to a solid substrate, including a bead or plastic membrane; is in a sterile composition; or is detectably labeled, including a radioactive or fluorescent label; or a natural DIRS2 polypeptide, wherein: the binding compound is in a container; the DIRS2 protein is from a human; the binding compound is an Fv, Fab, or Fab2 fragment; the binding compound is conjugated to another chemical moiety; or the antibody: is raised against a peptide sequence of a mature polypeptide of Table 2; is raised against a mature DIRS2; is raised to a purified human DIRS2; is immunoselected; is a polyclonal antibody; binds to a denatured DIRS2; exhibits a Kd to antigen of at least 30 µM; is attached to a solid substrate, including a bead or plastic membrane; is in a sterile composition; or is detectably labeled, including a radioactive or fluorescent label. Kit embodiments include, e.g., those comprising the binding compound, and: a compartment comprising the binding compound; or instructions for use or disposal of reagents in the kit.

Various methods are provided, e.g., of producing an antigen:antibody complex, comprising contacting under appropriate conditions: a primate DIRS1 polypeptide with a described antibody; or a primate DIRS2 polypeptide with a described antibody; thereby allowing the complex to form. In certain situations, the method is used wherein: the complex is purified from other interferon receptors; the complex is purified from other antibody; the contacting is with a sample comprising an interferon; the contacting allows quantitative detection of the antigen; the contacting is with a sample comprising the antibody; or the contacting allows quantitative detection of the antibody.

Other compositions comprise: a sterile binding compound as described, or the described binding compound and a carrier, wherein the carrier is: an aqueous compound, including water, saline, and/or buffer; and/or formulated for oral, rectal, nasal, topical, or parenteral administration.

Nucleic acid embodiments include, e.g., an isolated or recombinant nucleic acid encoding the: described DIRS1 polypeptide, wherein the: DIRS1 is from a human; or the nucleic acid: encodes an antigenic peptide sequence of Table 1; encodes a plurality of antigenic peptide sequences of Table 1; exhibits identity over at least thirteen nucleotides to a natural cDNA encoding the segment; is an expression vector; further comprises an origin of replication; is from a natural source; comprises a detectable label; comprises synthetic nucleotide sequence; is less than 6 kb, preferably less than 3 kb; is from a primate; comprises a natural full length coding sequence; is a hybridization probe for a gene encoding the DIRS1; or is a PCR primer, PCR product, or mutagenesis primer; or the described DIRS2 polypeptide, wherein the: DIRS2 is from a human; or the nucleic acid: encodes an antigenic peptide sequence of Table 2; encodes a plurality of antigenic peptide sequences of Table 2; exhibits identity over at least 30 nucleotides to a natural cDNA encoding the segment; is an expression vector; further comprises an origin of replication; is from a natural source; comprises a detectable label; comprises synthetic nucleotide sequence; is less than 6 kb, preferably less than 3 kb; is from a primate; comprises a natural full length coding sequence; is a hybridization probe for a gene encoding the DIRS2; or is a PCR primer, PCR product, or mutagenesis primer.

The invention further provides a cell or tissue comprising the described recombinant nucleic acid. Certain embodiments include wherein the cell is: a prokaryotic cell; a eukaryotic cell; a bacterial cell; a yeast cell; an insect cell; a mammalian cell; a mouse cell; a primate cell; or a human cell. Kits are also provided, e.g., the described nucleic acid and: a compartment comprising the nucleic acid; a compartment further comprising a primate DIRS1 polypeptide; a compartment further comprising a primate DIRS2 polypeptide; or instructions for use or disposal of reagents in the kit.

In other embodiments, the invention provides a nucleic acid which: hybridizes under wash conditions of 30 minutes at 30° C. and less than 2M salt to the coding portion of SEQ ID NO: 1; hybridizes under wash conditions of 30 minutes at 30° C. and less than 2M salt to the coding portion of SEQ ID NO: 3; exhibits identity over a stretch of at least about 30 nucleotides to a primate DIRS1 sequence; or exhibits identity over a stretch of at least about 30 nucleotides to a primate DIRS2 sequence. Preferred embodiments include those nucleic acids wherein: the wash conditions are at 45° C. and/or 500 mM salt; or the stretch is at least 55 nucleotides. Other embodiments include those nucleic acids wherein: the wash conditions are at 55° C. and/or 150 mM salt; or the stretch is at least 75 nucleotides.

The invention further provides a method of modulating physiology or development of a cell or tissue culture cells comprising contacting the cell with an agonist or antagonist of a mammalian DIRS1 or DIRS2. The method may involve where the cell is transformed with a nucleic acid encoding a DIRS1 or DIRS2 and another cytokine receptor subunit.

DETAILED DESCRIPTION OF THE PREFERRED EMBODIMENTS

Outline

I. General

II. Activities

III. Nucleic acids
  A. encoding fragments, sequence, probes
  B. mutations, chimeras, fusions
  C. making nucleic acids
  D. vectors, cells comprising IV. Proteins, Peptides
  A. fragments, sequence, immunogens, antigens
  B. muteins
  C. agonists/antagonists, functional equivalents
  D. making proteins V. Making nucleic acids, proteins
  A. synthetic
  B. recombinant
  C. natural sources VI. Antibodies
  A. polyclonals
  B. monoclonal
  C. fragments; Kd
  D. anti-idiotypic antibodies
  E. hybridoma cell lines VII. Kits and Methods to quantify DIRS
  A. ELISA
  B. assay mRNA encoding
  C. qualitative/quantitative
  D. kits VIII. Therapeutic compositions, methods
  A. combination compositions
  B. unit dose
  C. administration IX. Screening X. Ligands I. General The present invention provides the amino acid sequences and DNA sequences of mammalian, herein primate, interferon receptor-like subunit molecules, these ones designated DNAX Interferon Receptor family Subunit 1 (DIRS1) and DNAX Interferon Receptor family Subunit 2, having particular defined properties, both structural and biological. Various cDNAs encoding these molecules were obtained from primate, e.g., human, cDNA sequence libraries. Other primate or other mammalian counterparts would also be desired. Descriptions, methods, and manipulations directed to DIRS1 may be applied, as appropriate, to DIRS2.

Some of the standard methods applicable are described or referenced, e.g., in Maniatis, et al. (1982) *Molecular Cloning, A Laboratory Manual*, Cold Spring Harbor Laboratory, Cold Spring Harbor Press; Sambrook, et al. (1989) *Molecular Cloning: A Laboratory Manual*, (2d ed.), vols. 1-3, CSH Press, NY; Ausubel, et al., *Biology*, Greene Publishing Associates, Brooklyn, N.Y.; or Ausubel, et al. (1987 and periodic supplements) *Current Protocols in Molecular Biology*, Greene/Wiley, New York; each of which is incorporated herein by reference.

A partial nucleotide (SEQ ID NO: 1) and corresponding amino acid sequence (SEQ ID NO: 2) of a human DIRS1 coding segment is shown in Table 1. Partial human DIRS2 sequence is provided (SEQ ID NO: 3 and 4).

TABLE 1

Nucleotide and amino acid sequences of DNAX IFN Receptor Subunit like embodiments (DIRS1), originally designated HKAEF92.

```
TCGACCCACG CGTCCGCGCT GCGACTCAGA CCTCAGCTCC AACATATGCA TTCTGAAGAA    60

AGATGGCTGA GATGGACAGA ATGCTTTATT TTGGPAAGAA ACAATGTTCT AGGTCAAACT   120

GAGTCTACCA A ATG CAG ACT TTC ACA ATG GTT CTA GAA GAA ATC TGG ACA   170
            Met Gln Thr Phe Thr Met Val Leu Glu Glu Ile Trp Thr
            1               5                   10
```

TABLE 1-continued

Nucleotide and amino acid sequences of DNAX IFN Receptor Subunit like embodiments (DIRS1), originally designated HKAEF92.

```
AGT CTT TTC ATG TGG TTT TTC TAC GCA TTG ATT CCA TGT TTG CTC ACA    218
Ser Leu Phe Met Trp Phe Phe Tyr Ala Leu Ile Pro Cys Leu Leu Thr
 15              20                  25

GAT GAA GTG GCC ATT CTG CCT GCC CCT CAG AAC CTC TCT GTA CTC TCA    266
Asp Glu Val Ala Ile Leu Pro Ala Pro Gln Asn Leu Ser Val Leu Ser
 30              35                  40                  45

ACC AAC ATG AAG CAT CTC TTG ATG TGG AGC CCA GTG ATC GCG CCT GGA    314
Thr Asn Met Lys His Leu Leu Met Trp Ser Pro Val Ile Ala Pro Gly
                 50                  55                  60

GAA ACA GTG TAC TAT TCT GTC GAA TAC CAG GGG GAG TAC GAG AGC CTG    362
Glu Thr Val Tyr Tyr Ser Val Glu Tyr Gln Gly Glu Tyr Glu Ser Leu
                     65                  70                  75

TAC ACG AGC CAC ATC TGG ATC CCC AGC AGC TGG TGC TCA CTC ACT GAA    410
Tyr Thr Ser His Ile Trp Ile Pro Ser Ser Trp Cys Ser Leu Thr Glu
             80                  85                  90

GGT CCT GAG TGT GAT GTC ACT GAT GAC ATC ACG GCC ACT GTG CCA TAC    458
Gly Pro Glu Cys Asp Val Thr Asp Asp Ile Thr Ala Thr Val Pro Tyr
 95                 100                 105

AAC CTT CGT GTC AGG GCC ACA TTG GGC TCA CAG ACC TCA GCC TGG AGC    506
Asn Leu Arg Val Arg Ala Thr Leu Gly Ser Gln Thr Ser Ala Trp Ser
110                 115                 120                 125

ATC CTG AAG CAT CCC TTT AAT AGA AAC TCA ACC ATC CTT ACC CGA CCT    554
Ile Leu Lys His Pro Phe Asn Arg Asn Ser Thr Ile Leu Thr Arg Pro
                130                 135                 140

GGG ATG GAG ATC CCC PAA CAT GGC TTC CAC CTG GTT ATT GAG CTG GAG    602
Gly Met Glu Ile Pro Lys His Gly Phe His Leu Val Ile Glu Leu Glu
                145                 150                 155

GAC CTG GGG CCC CAG TTT GAG TTC CTT GTG GCC TAC TGG ACG AGG GAG    650
Asp Leu Gly Pro Gln Phe Glu Phe Leu Val Ala Tyr Trp Thr Arg Glu
                160                 165                 170

CCT GGT GCC GAG GAA CAT GTC AAA ATG GTG AGG AGT GGG GGT ATT CCA    698
Pro Gly Ala Glu Glu His Val Lys Met Val Arg Ser Gly Gly Ile Pro
175                 180                 185

GTG CAC CTA GAA ACC ATG GAG CCA GGG GCT GCA TAC TGT GTG AAG GCC    746
Val His Leu Glu Thr Met Glu Pro Gly Ala Ala Tyr Cys Val Lys Ala
190                 195                 200                 205

CAG ACA TTC GTG AAG GCC ATT GGG AGG TAC AGC GCC TTC AGC CAG ACA    794
Gln Thr Phe Val Lys Ala Ile Gly Arg Tyr Ser Ala Phe Ser Gln Thr
                210                 215                 220

GAA TGT GTG GAG GTG CAA GGA GAG GCC ATT CCC CTG GTA CTG GCC CTG    842
Glu Cys Val Glu Val Gln Gly Glu Ala Ile Pro Leu Val Leu Ala Leu
                225                 230                 235

TTT GCC TTT GTT GGC TTC ATG CTG ATC CTT GTG GTC GTG CCA CTG TTC    890
Phe Ala Phe Val Gly Phe Met Leu Ile Leu Val Val Val Pro Leu Phe
                240                 245                 250

GTC TGG AAA ATG GGC CGG CTG CTC CAG TAC TCC TGT TGC CCC GTG GTG    938
Val Trp Lys Met Gly Arg Leu Leu Gln Tyr Ser Cys Cys Pro Val Val
255                 260                 265

GTC CTC CCA GAC ACC TTG AAA ATA ACC AAT TCA CCC CAG AAG TTA ATC    986
Val Leu Pro Asp Thr Leu Lys Ile Thr Asn Ser Pro Gln Lys Leu Ile
270                 275                 280                 285

AGC TGC AGA AGG GAG GAG GTG GAT GCC TGT GCC ACG GCT GTG ATG TCT   1034
Ser Cys Arg Arg Glu Glu Val Asp Ala Cys Ala Thr Ala Val Met Ser
                290                 295                 300

CCT GAG GAA CTC CTC AGG GCC TGG ATC TCA TAGGTTTGCG GAAGGGCCCA     1084
Pro Glu Glu Leu Leu Arg Ala Trp Ile Ser
                305                 310
```

TABLE 1-continued

Nucleotide and amino acid sequences of DNAX IFN Receptor
Subunit like embodiments (DIRS1), originally designated HKAEF92.

```
GGTGAAGCCG AGAACCTGGT CTGCATGACA TGGAAACCAT GAGGGGACAA GTTGTGTTTC   1144

TGTTTTCCGC CACGGACAAG GGATGAGAGA AGTAGGAAGA GCCTGTTGTC TACAAGTCTA   1204

GAAGCAACCA TCAGAGGCAG GGTGGTTTGT CTAACAGAAC AACTGACTGA GGCTATGGGG   1264

GTTGTGACCT CTAGACTTTG GGCTTCCACT TGCTTGGCTG AGCAACCCTG GGAAAAGTGA   1324

CTTCATCCCT TCGGTCCCAA GTTTTCTCAT CTGTAATGGG GGATCCCTAC AAAACTG     1381
```

Primate, e.g., human embodiment (see SEQ ID NO: 1 and 2).
Nucleotides 567, 573, 1336, 1342, and 1369 are designated C, but may be A, C, G, or T;
nucleotides 643, 1287, and 1290 are designated C, but may be C or G;
nucleotides 772, 806, and 1261 are designated G, but may be A or G;
nucleotides 1236, 1260, 1282, and 1289 are designated U, but may be G or T;
residues 1247, 1257, 1293, and 1302 are designated C, but may be C or T; and
nucleotides 1266 and 1298 are designated T, but may be A or T.
Additional sequencing indicates that nucleotide 567 is A; 574 is G; 640 is G; 742 is
G; and 806 is G. Predicted signal cleavage is about between thr29 and asp30.

TABLE 2

Partial nucleotide and amino acid sequences of DNAX IFN Receptor
Subunit like embodiments (DIRS2), originally designated HOFNY28
(SEQ ID NO: 3 and 4).

```
  C CGG GTC GAC CCA CGC GTC CGC CTG GTT TCC CCC TGG CTG ACA GTG        46
    Arg Val Asp Pro Arg Val Arg Leu Val Ser Pro Trp Leu Thr Val
     1               5                  10                  15

CCT TGG TTC CTG TCC TGT TGG AAT GTT ACC ATT GGG CCT CCT GAG AGC        94
Pro Trp Phe Leu Ser Cys Trp Asn Val Thr Ile Gly Pro Pro Glu Ser
                    20                  25                  30

ATC TGG GTG ACG CCG GGA GAA GCC TCC CTC ATC ATC AGG TTC TCC TCT       142
Ile Trp Val Thr Pro Gly Glu Ala Ser Leu Ile Ile Arg Phe Ser Ser
                35                  40                  45

CCC TTC GAC GTC CCT CCC AAC CTG GGC TAT TTC CAG TAC TAT GTC CAT       190
Pro Phe Asp Val Pro Pro Asn Leu Gly Tyr Phe Gln Tyr Tyr Val His
            50                  55                  60

TAC TGG GAA AAG GCG GGA ATC CAA AAG GTT AAA GGT CCT TTC AAG AGC       238
Tyr Trp Glu Lys Ala Gly Ile Gln Lys Val Lys Gly Pro Phe Lys Ser
 65                  70                  75

AAC TCC ATC GTG TTG GAT GGC TTG AGA CCC TTA AGA GAA TAC TGT TTA       286
Asn Ser Ile Val Leu Asp Gly Leu Arg Pro Leu Arg Glu Tyr Cys Leu
 80                  85                  90                  95

CAA GTG AAG GCG CAT CTC TTT CGC ACA TCC TGC AAC ACC TCT AGG CCC       334
Gln Val Lys Ala His Leu Phe Arg Thr Ser Cys Asn Thr Ser Arg Pro
                    100                 105                 110

GGC CGC TTA AGC AAC ATA ACT TGC TAC GAA ACA ATG ATG GAT GCC ACT       382
Gly Arg Leu Ser Asn Ile Thr Cys Tyr Glu Thr Met Met Asp Ala Thr
                115                 120                 125

ACG AAG CTT CAA CAA GTC ATC CTC ATC GCC GTG GGA GTC TTT CTG TCG       430
Thr Lys Leu Gln Gln Val Ile Leu Ile Ala Val Gly Val Phe Leu Ser
            130                 135                 140

CTG GCG GCG CTG GCG GGG GGC TGT TTC TTC CTG GTG CTG AGA TAC AAA       478
Leu Ala Ala Leu Ala Gly Gly Cys Phe Phe Leu Val Leu Arg Tyr Lys
        145                 150                 155

GGC CTG GTG AAA TAC TGG TTT CAC TCT CCG CCA AGC ATC CCA TCA CAA       526
Gly Leu Val Lys Tyr Trp Phe His Ser Pro Pro Ser Ile Pro Ser Gln
160                 165                 170                 175

ATC GAA GAG TAT CTG AAG GAC CCG AGC CAG CCT ATC CTA GAG GCC CTG       574
Ile Glu Glu Tyr Leu Lys Asp Pro Ser Gln Pro Ile Leu Glu Ala Leu
                    180                 185                 190
```

TABLE 2-continued

Partial nucleotide and amino acid sequences of DNAX IFN Receptor
Subunit like embodiments (DIRS2), originally designated HOFNY28
(SEQ ID NO: 3 and 4).

```
GAC AAG GAC ACG TCA CCA ACA GAT GAT GCC TGG GAC TTG GTG TCT GTT    622
Asp Lys Asp Thr Ser Pro Thr Asp Asp Ala Trp Asp Leu Val Ser Val
            195                 200                 205

GTT GCA TTT CCA GCA AAG GAG CAA GAA GAT GTT CCC CAA AGC ACT TTG    670
Val Ala Phe Pro Ala Lys Glu Gln Glu Asp Val Pro Gln Ser Thr Leu
            210                 215                 220

ACC CAA AAC TCT GGT GCG GTC TGC TAGCCTGTGG GGTAAGGGCT CTGAGCCGAG   724
Thr Gln Asn Ser Gly Ala Val Cys
            225             230

GAAGCTGCTG ATGTCCATGT CAGCACTTTA TGGAATCCGG TCCTCCATTT TCCTGTCCCC   784

AAAAGGCCCG TCAGTGCCTG TGAAGATGTA ACGGGTCTCA TGGGGCGAC AAGCTTATTG    844

ATTTTTTTCT TCAAACTAAG AGTTTTCTAA TCATACGCGT TTTTAGAATA ATTCTACAGA   904

TATGTCCCCG AAAGATTAAG ATTTCTCTTA AACACTAAAA AGACATGTAA TTATTTGTTA   964

GCAAATGGGC GTCTGGCACG CCTCTGACAC TTTTTCGTCA GCAGCCAGGA CACGAGGTCC  1024

CCTCCTTGAT GAAGCCCCTC GGGCAGACCA TGTCACCTGT CCCAGCCTGC CCCAAGAAGG  1084

GACATTAAGT GGCCCTTCTT CATATCCAAA CACCTGGCTT GAAATGTGAT TAGCCCTGTA  1144

AATAGTTTCA CAGAGATTAA GCCTTTTTTT CCCCCAAGTT AGGAATAAAA GACTATAATT  1204

AACTTTTTAA AAAAAAAAA AAAAAAAAA AAAAAAAAA                         1244
```

Nucleotide 193 designated C, may be C or T; additional sequencing indicates that
nucleotide is C.

TABLE 3

Sequence alignment of related IFN receptor family members.

```
DR2 ---------- ---------- ---------- -------RVD PRVRLV---- ----------
DR1 MQTFTMVLEE IWTSLFMWFF YALIPCLLTD EVAILPAPQN LSVLSTNMKH LLMWSPVIAP
IRβ -----MRPTL LWSLLLLLGV FAAAAAPPD PLSQLPAPQH PKIRLYNAEQ VLSWEPVALS
crf ---------M AWSLGSWLGG CLLVSALG-- ---MVPPPEN VRMNSVNFKN ILQWESPAFA DR2 ---------- ---------- ---------- ---------- ---------- -------SP
DR1 GETVYYSVEY QGEYES--LY TSHIWIPSSW CSLTEGPECD VTDDITAT-- ---VPYNLRV
IRβ NSTRPVVYRV QFKYTDSKWF TADIMSIGVN CTQITATECD FTAASPSAGF PMDFNVTLRL
crf KGNLTFTAQY LSYR------ -----IFQDK CMNTTLTECD FSSLSKYG-- ----DHTLRV DR2 WLTVPWFLSC WNVTIGPPES IWVTPGEASL IIRFSSPFDV PPN------- -LGYFQYVVH
DR1 RATLGSQTSA WSILK-HPFN RNSTILTRPG MEIXKXGFHL VIELE---DL GPQ-------
IRβ RAELGALHSA WVTMPWFQHY RNVTVGPPEN IEVTPGEGSL IIRFSSPFDI ADTS------
crf RAEFADEHSD WVNIT-FCPV DDTIIGPP-G MQVEVLADSL HMRFLAPKIE NEYETWTMKN DR2 YW--EKAGIQ KVKGPFKSNS -IVLDGLRPL REYCLQVKAH LFRTSCNTSR PGRLSNITCY
DR1 ----FEFLVA YWXREPGAEE HVKMVRSGGI PVHLETMEPG AAYCVKAQT- -FVKAIGX--
IRβ -TAFFCYYVH Y--WEKGGIQ QVKGPFRSNS -ISLDNLKPS RVYCLQVQAQ LLWNKSNIFR
crf VYNSWTYNVQ YW--KNGTDE KFQITPQYDF -EVLRNLEPW TTYCVQVRG- -FLPDRNK--

DR2 ETMMDATTKL QQVILIAVGV FLSLAALAGG CFFLVLRYKG LVKYWFHSPP SIPSQIEEYL
DR1 YSAFSQTECV EVQG-EAIPL VLALFAFVG- -FMLILVVVP LF--VWKMGR LLQYSCCPVV
IRβ VGHLSNISCY ETMADASTEL QQVILISVGT FSLLSVLAGA CFFLVLKYRG LIKYWFHTPP
crf AGEWSEPVCE QTTHDETVPS WMVAVILMAS VFMVCLALLG CFSLLWCVYK KTKYAFSPRN DR2 KDPSQPILEA LDKDTSPTDD AWDLVSVVAF PAK--EQE-- DVPQSTLTQN
DR1 VLPDTLKITN S-P-QKLISC R----REEVD AC--ATAVMS PEE-------
IRβ SIPLQIEEYL KDPTQPILEA LDKDSSPKDD VWDSVSIISF PEK--EQE--
crf SLPQHLKEFL GHPHHNTLLF FSFPLSDEND VFDKLSVIAE DSESGKQNPG

DR2 SGAVC
DR1 -LLRAWIS
```

TABLE 3-continued

Sequence alignment of related IFN receptor family members.

```
IRβ DVLQTL
crf DSCSLGTPPG QGPQS
```

DR1 is a primate DIRS1 protein sequence; DR2 is a primate DIRS2 protein sequence; the IRβ is the human IFN-γ receptor beta subunit (SEQ ID NO: 5), see Soh, et al. (1994) Cell 76:793-802; and CRF is the crf2-4 protein (SEQ ID NO: 6), see Lutfalla, et al. (1993) Genomics 16:366-373:

Table 3 shows comparison of the available sequences of primate embodiments of DIRS1, DIRS2, and two related interferon receptor family members. Both of the new DIRS appear to exhibit sequence similarity to beta interferon receptor subunits.

Structural features of the human DIRS1, and similarly for the other receptors as aligned in Table 3, include characteristic transmembrane segments of the IRβ and crf from 261-273, and correspond to: from about val1 to pro133; fibronectin domains corresponding to the DIRS1 sequence from about gly134 to pro232, gly233 to gly306, and pro307 to lys403; a transmembrane segment from about val404 to gly427; and an intracellular domain from about arg428 to the carboxy terminus. Of particular interest is the WGEWS motif corresponding to residues trp104 to ser108.

As used herein, the term DIRS1 shall be used to describe a protein comprising a protein or peptide segment having or sharing the amino acid sequence shown in Table 1, or a substantial fragment thereof. The invention also includes a protein variation of the respective DIRS1 allele whose sequence is provided, e.g., a mutein or soluble extracellular construct. Typically, such agonists or antagonists will exhibit less than about 10% sequence differences, and thus will often have between 1- and 11-fold substitutions, e.g., 2-, 3-, 5-, 7-fold, and others. It also encompasses allelic and other variants, e.g., natural polymorphic, of the protein described. Typically, it will bind to its corresponding biological ligand, perhaps in a dimerized state with an alpha receptor subunit, with high affinity, e.g., at least about 100 nM, usually better than about 30 nM, preferably better than about 10 nM, and more preferably at better than about 3 nM. The term shall also be used herein to refer to related naturally occurring forms, e.g., alleles, polymorphic variants, and metabolic variants of the mammalian protein.

This invention also encompasses proteins or peptides having substantial amino acid sequence identity with the amino acid sequence in Table 1. It will include sequence variants with relatively few substitutions, e.g., preferably less than about 3-5. Other embodiments include forms in association with an alpha subunit, e.g., a DSRS1, and/or with ligand, e.g., DIL-30.

A substantial polypeptide "fragment", or "segment", is a stretch of amino acid residues of at least about 8 amino acids, generally at least 10 amino acids, more generally at least 12 amino acids, often at least 14 amino acids, more often at least 16 amino acids, typically at least 18 amino acids, more typically at least 20 amino acids, usually at least 22 amino acids, more usually at least 24 amino acids, preferably at least 26 amino acids, more preferably at least 28 amino acids, and, in particularly preferred embodiments, at least about 30 or more amino acids, e.g., 35, 40, 50, 70, 90, 110, etc. Specific ends may be at all possible or appropriate combinations, or at proline residues. Sequences of segments of different proteins can be compared to one another over appropriate length stretches.

The invention provides polypeptides exhibiting a plurality of distinct, e.g., nonoverlapping, segments of the specified length. Typically, the plurality will be at least two, more usually at least three, and preferably 5, 7, or even more. While the length minima are provided, longer lengths, of various sizes, may be appropriate, e.g., one of length 7, and two of length 12.

Amino acid sequence homology, or sequence identity, is determined by optimizing residue matches. In some comparisons, gaps may be introduces, as required. See, e.g., Needleham, et al. (1970) *J. Mol. Biol.* 48:443-453; Sankoff, et al., (1983) chapter one in *Time Warps, String Edits, and Macromolecules: The Theory and Practice of Sequence Comparison*, Addison-Wesley, Reading, Mass.; and software packages from NCBI, NIH; and the University of Wisconsin Genetics Computer Group (GCG), Madison, Wis.; each of which is incorporated herein by reference. This changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Homologous amino acid sequences are intended to include natural allelic and interspecies variations in the cytokine sequence. Typical homologous proteins or peptides will have from 50-100% homology (if gaps can be introduced), to 60-100% homology (if conservative substitutions are included) with an amino acid sequence segment of Table 1. Homology measures will be at least about 70%, generally at least 76%, more generally at least 81%, often at least 85%, more often at least 88%, typically at least 90%, more typically at least 92%, usually at least 94%, more usually at least 95%, preferably at least 96%, and more preferably at least 97%, and in particularly preferred embodiments, at least 98% or more. The degree of homology will vary with the length of the compared segments. Homologous proteins or peptides, such as the allelic variants, will share most biological activities with the embodiments described in Table 1.

As used herein, the term "biological activity" is used to describe, without limitation, effects on inflammatory responses, innate immunity, and/or morphogenic development by cytokine-like ligands. For example, these receptors should mediate phosphatase or phosphorylase activities, which activities are easily measured by standard procedures. See, e.g., Hardie, et al. (eds. 1995) *The Protein Kinase Fact-Book* vols. I and II, Academic Press, San Diego, Calif.; Hanks, et al. (1991) *Meth. Enzymol.* 200:38-62; Hunter, et al. (1992) *Cell* 70:375-388; Lewin (1990) *Cell* 61:743-752; Pines, et al. (1991) *Cold Spring Harbor Symp. Quant. Biol.* 56:449-463; and Parker, et al. (1993) *Nature* 363:736-738. The receptors, or portions thereof, may be useful as phosphate labeling enzymes to label general or specific substrates.

The terms ligand, agonist, antagonist, and analog of, e.g., a DIRS1, include molecules that modulate the characteristic cellular responses to cytokine ligand proteins, as well as molecules possessing the more standard structural binding competition features of ligand-receptor interactions, e.g., where the receptor is a natural receptor or an antibody. The cellular responses likely are typically mediated through receptor tyrosine kinase pathways.

Also, a ligand is a molecule which serves either as a natural ligand to which said receptor, or an analog thereof, binds, or a molecule which is a functional analog of the natural ligand. The functional analog may be a ligand with structural modifications, or may be a wholly unrelated molecule which has a molecular shape which interacts with the appropriate ligand binding determinants. The ligands may serve as agonists or antagonists, see, e.g., Goodman, et al. (eds. 1990) *Goodman & Gilman's: The Pharmacological Bases of Therapeutics*, Pergamon Press, New York.

Rational drug design may also be based upon structural studies of the molecular shapes of a receptor or antibody and other effectors or ligands. See, e.g., Herz, et al. (1997) *J. Recept. Signal Transduct. Res.* 17:671-776; and Chaiken, et al. (1996) *Trends Biotechnol.* 14:369-375. Effectors may be other proteins which mediate other functions in response to ligand binding, or other proteins which normally interact with the receptor. One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) *Protein Crystallography*, Academic Press, New York, which is hereby incorporated herein by reference.

II. Activities

The cytokine receptor-like proteins will have a number of different biological activities, e.g., modulating cell proliferation, or in phosphate metabolism, being added to or removed from specific substrates, typically proteins. Such will generally result in modulation of an inflammatory function, other innate immunity response, or a morphological effect. The subunit will probably have a specific low affinity binding to the ligand.

The DIRS1 has the characteristic motifs of a receptor signaling through the JAK pathway. See, e.g., Ihle, et al. (1997) *Stem Cells* 15(suppl. 1):105-111; Silvennoinen, et al. (1997) *APMIS* 105:497-509; Levy (1997) *Cytokine Growth Factor Review* 8:81-90; Winston and Hunter (1996) *Current Biol.* 6:668-671; Barrett (1996) *Baillieres Clin. Gastroenterol.* 10:1-15; and Briscoe, et al. (1996) *Philos. Trans. R. Soc. Lond. B. Biol. Sci.* 351:167-171.

The biological activities of the cytokine receptor subunits will be related to addition or removal of phosphate moieties to substrates, typically in a specific manner, but occasionally in a non specific manner. Substrates may be identified, or conditions for enzymatic activity may be assayed by standard methods, e.g., as described in Hardie, et al. (eds. 1995) *The Protein Kinase FactBook* vols. I and II, Academic Press, San Diego, Calif.; Hanks, et al. (1991) *Meth. Enzymol.* 200:38-62; Hunter, et al. (1992) *Cell* 70:375-388; Lewin (1990) *Cell* 61:743-752; Pines, et al. (1991) *Cold Spring Harbor Symp. Quant. Biol.* 56:449-463; and Parker, et al. (1993) *Nature* 363:736-738.

III. Nucleic Acids

This invention contemplates use of isolated nucleic acid or fragments, e.g., which encode these or closely related proteins, or fragments thereof, e.g., to encode a corresponding polypeptide, preferably one which is biologically active. In addition, this invention covers isolated or recombinant DNAs which encode such proteins or polypeptides having characteristic sequences of the DIRS1s. Typically, the nucleic acid is capable of hybridizing, under appropriate conditions, with a nucleic acid sequence segment shown in Table 1, but preferably not with a corresponding segment of other receptors described in Table 3. Said biologically active protein or polypeptide can be a full length protein, or fragment, and will typically have a segment of amino acid sequence highly homologous, e.g., exhibiting significant stretches of identity, to one shown in Table 1. Further, this invention covers the use of isolated or recombinant nucleic acid, or fragments thereof, which encode proteins having fragments which are equivalent to the DIRS1 proteins. The isolated nucleic acids can have the respective regulatory sequences in the 5' and 3' flanks, e.g., promoters, enhancers, poly-A addition signals, and others from the natural gene.

An "isolated" nucleic acid is a nucleic acid, e.g., an RNA, DNA, or a mixed polymer, which is substantially pure, e.g., separated from other components which naturally accompany a native sequence, such as ribosomes, polymerases, and flanking genomic sequences from the originating species. The term embraces a nucleic acid sequence which has been removed from its naturally occurring environment, and includes recombinant or cloned DNA isolates, which are thereby distinguishable from naturally occurring compositions, and chemically synthesized analogs or analogs biologically synthesized by heterologous systems. A substantially pure molecule includes isolated forms of the molecule, either completely or substantially pure.

An isolated nucleic acid will generally be a homogeneous composition of molecules, but will, in some embodiments, contain heterogeneity, preferably minor. This heterogeneity is typically found at the polymer ends or portions not critical to a desired biological function or activity.

A "recombinant" nucleic acid is typically defined either by its method of production or its structure. In reference to its method of production, e.g., a product made by a process, the process is use of recombinant nucleic acid techniques, e.g., involving human intervention in the nucleotide sequence. Typically this intervention involves in vitro manipulation, although under certain circumstances it may involve more classical animal breeding techniques. Alternatively, it can be a nucleic acid made by generating a sequence comprising fusion of two fragments which are not naturally contiguous to each other, but is meant to exclude products of nature, e.g., naturally occurring mutants as found in their natural state. Thus, for example, products made by transforming cells with an unnaturally occurring vector is encompassed, as are nucleic acids comprising sequence derived using any synthetic oligonucleotide process. Such a process is often done to replace a codon with a redundant codon encoding the same or a conservative amino acid, while typically introducing or removing a restriction enzyme sequence recognition site. Alternatively, the process is performed to join together nucleic acid segments of desired functions to generate a single genetic entity comprising a desired combination of functions not found in the commonly available natural forms, e.g., encoding a fusion protein. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. This will include a dimeric repeat. Specifically included are synthetic nucleic acids which, by genetic code redundancy, encode equivalent polypeptides to fragments of DIRS1 and fusions of sequences from various different related molecules, e.g., other cytokine receptor family members.

A "fragment" in a nucleic acid context is a contiguous segment of at least about 17 nucleotides, generally at least 21 nucleotides, more generally at least 25 nucleotides, ordinarily at least 30 nucleotides, more ordinarily at least 35 nucleotides, often at least 39 nucleotides, more often at least 45 nucleotides, typically at least 50 nucleotides, more typically at least 55 nucleotides, usually at least 60 nucleotides, more usually at least 66 nucleotides, preferably at least 72 nucleotides, more preferably at least 79 nucleotides, and in particularly preferred embodiments will be at least 85 or more nucleotides. Typically, fragments of different genetic sequences can be compared to one another over appropriate length stretches, particularly defined segments such as the domains described below.

A nucleic acid which codes for a DIRS1 will be particularly useful to identify genes, mRNA, and cDNA species which code for itself or closely related proteins, as well as DNAs which code for polymorphic, allelic, or other genetic variants, e.g., from different individuals or related species. Preferred probes for such screens are those regions of the interleukin which are conserved between different polymorphic variants or which contain nucleotides which lack specificity, and will preferably be full length or nearly so. In other situations, polymorphic variant specific sequences will be more useful.

This invention further covers recombinant nucleic acid molecules and fragments having a nucleic acid sequence identical to or highly homologous to the isolated DNA set forth herein. In particular, the sequences will often be operably linked to DNA segments which control transcription, translation, and DNA replication. These additional segments typically assist in expression of the desired nucleic acid segment.

Homologous, or highly identical, nucleic acid sequences, when compared to one another, e.g., DIRS1 sequences, exhibit significant similarity. The standards for homology in nucleic acids are either measures for homology generally used in the art by sequence comparison or based upon hybridization conditions. Comparative hybridization conditions are described in greater detail below.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optical alignment of sequences for comparison can be conducted, e.g., by the local homology algorithm of Smith and Waterman (1981) *Adv. Appl. Math.* 2:482, by the homology alignment algorithm of Needleman and Wunsch (1970) *J. Mol. Biol.* 48:443, by the search for similarity method of Pearson and Lipman (1988) *Proc. Nat'l Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendrogram showing the clustering relationships used to create the alignment. PILEUP uses a simplification of the progressive alignment method of Feng and Doolittle (1987) *J. Mol. Evol.* 35:351-360. The method used is similar to the method described by Higgins and Sharp (1989) *CABIOS* 5:151-153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of an algorithm that is suitable for determining percent sequence identity and sequence similarity is the BLAST algorithm, which is described Altschul, et al. (1990) *J. Mol. Biol.* 215:403-410. Software for performing BLAST analyses is publicly available through the National Center for Biotechnology Information on the world wide web at "ncbi.nlm.nih.gov." This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul, et al., supra). These initial neighborhood word hits act as seeds for initiating searches to find longer HSPs containing them. The word hits are then extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff and Henikoff (1989) *Proc. Nat'l Acad. Sci. USA* 89:10915) alignments (B) of 50, expectation (E) of 10, M=5, N=4, and a comparison of both strands.

In addition to calculating percent sequence identity, the BLAST algorithm also performs a statistical analysis of the similarity between two sequences (see, e.g., Karlin and Altschul (1993) *Proc. Nat'l Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences of polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below. Hybridization under stringent conditions should give a background of at least 2-fold over background, preferably at least 3-5 or more.

Substantial identity in the nucleic acid sequence comparison context means either that the segments, or their complementary strands, when compared, are identical when optimally aligned, with appropriate nucleotide insertions or deletions, in at least about 60% of the nucleotides, generally at least 66%, ordinarily at least 71%, often at least 76%, more often at least 80%, usually at least 84%, more usually at least 88%, typically at least 91%, more typically at least about 93%, preferably at least about 95%, more preferably at least about 96 to 98% or more, and in particular embodiments, as high at about 99% or more of the nucleotides, including, e.g., segments encoding structural domains such as the segments described below. Alternatively, substantial identity will exist when the segments will hybridize under selective hybridization conditions, to a strand or its complement, typically using a sequence derived from Table 1. Typically, selective hybridization will occur when there is at least about 55% homology over a stretch of at least about 14 nucleotides, more typically at least about 65%, preferably at least about 75%, and more preferably at least about 90%. See, Kanehisa (1984) *Nucl. Acids Res.* 12:203-213, which is incorporated herein by reference. The length of homology comparison, as described, may be over longer stretches, and in certain embodiments will be over a stretch of at least about 17 nucleotides, generally at least about 20 nucleotides, ordinarily at least about 24 nucleotides, usually at least about 28 nucleotides, typically at least about 32 nucleotides, more typically at least about 40 nucleotides, preferably at least about 50 nucleotides, and more preferably at least about 75 to 100 or more nucleotides. This includes, e.g., 125, 150, 175, 200, 225, 246, 273, and other lengths.

Stringent conditions, in referring to homology in the hybridization context, will be stringent combined conditions of salt, temperature, organic solvents, and other parameters typically controlled in hybridization reactions. Stringent temperature conditions will usually include temperatures in excess of about 30° C., more usually in excess of about 37° C., typically in excess of about 45° C., more typically in excess of about 55° C., preferably in excess of about 65° C., and more preferably in excess of about 70° C. Stringent salt conditions will ordinarily be less than about 500 mM, usually less than about 400 mM, more usually less than about 300 mM, typically less than about 200 mM, preferably less than about 100 mM, and more preferably less than about 80 mM, even down to less than about 20 mM. However, the combination of parameters is much more important than the measure of any single parameter. See, e.g., Wetmur and Davidson (1968) *J. Mol. Biol.* 31:349-370, which is hereby incorporated herein by reference.

The isolated DNA can be readily modified by nucleotide substitutions, nucleotide deletions, nucleotide insertions, and inversions of nucleotide stretches. These modifications result in novel DNA sequences which encode this protein or its derivatives. These modified sequences can be used to produce mutant proteins (muteins) or to enhance the expression of variant species. Enhanced expression may involve gene amplification, increased transcription, increased translation, and other mechanisms. Such mutant DIRS1-like derivatives include predetermined or site-specific mutations of the protein or its fragments, including silent mutations using genetic code degeneracy. "Mutant DIRS1" as used herein encompasses a polypeptide otherwise falling within the homology definition of the DIRS1 as set forth above, but having an amino acid sequence which differs from that of other cytokine receptor-like proteins as found in nature, whether by way of deletion, substitution, or insertion. In particular, "site specific mutant DIRS1" encompasses a protein having substantial sequence identity with a protein of Table 1, and typically shares most of the biological activities or effects of the forms disclosed herein.

Although site specific mutation sites are predetermined, mutants need not be site specific. Mammalian DIRS1 mutagenesis can be achieved by making amino acid insertions or deletions in the gene, coupled with expression. Substitutions, deletions, insertions, or many combinations may be generated to arrive at a final construct. Insertions include amino- or carboxy-terminal fusions. Random mutagenesis can be conducted at a target codon and the expressed mammalian DIRS1 mutants can then be screened for the desired activity, providing some aspect of a structure-activity relationship. Methods for making substitution mutations at predetermined sites in DNA having a known sequence are well known in the art, e.g., by M13 primer mutagenesis. See also Sambrook, et al. (1989) and Ausubel, et al. (1987 and periodic Supplements).

The mutations in the DNA normally should not place coding sequences out of reading frames and preferably will not create complementary regions that could hybridize to produce secondary mRNA structure such as loops or hairpins.

The phosphoramidite method described by Beaucage and Carruthers (1981) *Tetra. Letts.* 22:1859-1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence.

Polymerase chain reaction (PCR) techniques can often be applied in mutagenesis. Alternatively, mutagenesis primers are commonly used methods for generating defined mutations at predetermined sites. See, e.g., Innis, et al. (eds. 1990) *PCR Protocols: A Guide to Methods and Applications* Academic Press, San Diego, Calif.; and Dieffenbach and Dveksler (eds. 1995) *PCR Primer: A Laboratory Manual* Cold Spring Harbor Press, CSH, NY.

IV. Proteins, Peptides

As described above, the present invention encompasses primate DIRS1, e.g., whose sequences are disclosed in Table 1, and described above. Allelic and other variants are also contemplated, including, e.g., fusion proteins combining portions of such sequences with others, including epitope tags and functional domains.

The present invention also provides recombinant proteins, e.g., heterologous fusion proteins using segments from these rodent proteins. A heterologous fusion protein is a fusion of proteins or segments which are naturally not normally fused in the same manner. Thus, the fusion product of a DIRS1 with another cytokine receptor is a continuous protein molecule having sequences fused in a typical peptide linkage, typically made as a single translation product and exhibiting properties, e.g., sequence or antigenicity, derived from each source peptide. A similar concept applies to heterologous nucleic acid sequences.

In addition, new constructs may be made from combining similar functional or structural domains from other related proteins, e.g., cytokine receptors or Toll-like receptors, including species variants. For example, ligand-binding or other segments may be "swapped" between different new fusion polypeptides or fragments. See, e.g., Cunningham, et al. (1989) *Science* 243:1330-1336; and O'Dowd, et al. (1988) *J. Biol. Chem.* 263:15985-15992, each of which is incorporated herein by reference. Thus, new chimeric polypeptides exhibiting new combinations of specificities will result from the functional linkage of receptor-binding specificities. For example, the ligand binding domains from other related receptor molecules may be added or substituted for other domains of this or related proteins. The resulting protein will often have hybrid function and properties. For example, a fusion protein may include a targeting domain which may serve to provide sequestering of the fusion protein to a particular subcellular organelle.

Candidate fusion partners and sequences can be selected from various sequence data bases, e.g., GenBank; NCBI, NIH; and BCG, University of Wisconsin Biotechnology Computing Group, Madison, Wis., which are each incorporated herein by reference.

The present invention particularly provides muteins which bind cytokine-like ligands, and/or which are affected in signal transduction. Structural alignment of human DIRS1 with other members of the cytokine receptor family show conserved features/residues. See Table 3. Alignment of the human DIRS1 sequence with other members of the cytokine receptor family indicates various structural and functionally shared features. See also, Bazan, et al. (1996) *Nature* 379: 591; Lodi, et al. (1994) *Science* 263:1762-1766; Sayle and Milner-White (1995) *TIBS* 20:374-376; and Gronenberg, et al. (1991) *Protein Engineering* 4:263-269.

Substitutions with either mouse sequences or human sequences are particularly preferred. Conversely, conservative substitutions away from the ligand binding interaction regions will probably preserve most signaling activities; and conservative substitutions away from the intracellular domains will probably preserve most ligand binding properties.

"Derivatives" of the primate DIRS1 include amino acid sequence mutants, glycosylation variants, metabolic derivatives and covalent or aggregative conjugates with other chemical moieties. Covalent derivatives can be prepared by linkage of functionalities to groups which are found in the DIRS1 amino acid side chains or at the N- or C-termini, e.g., by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues, e.g., lysine or arginine. Acyl groups are selected from the group of alkyl-moieties, including C3 to C18 normal alkyl, thereby forming alkanoyl aroyl species.

In particular, glycosylation alterations are included, e.g., made by modifying the glycosylation patterns of a polypeptide during its synthesis and processing, or in further processing steps. Particularly preferred means for accomplishing this are by exposing the polypeptide to glycosylating enzymes derived from cells which normally provide such processing, e.g., mammalian glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine.

A major group of derivatives are covalent conjugates of the receptors or fragments thereof with other proteins of polypeptides. These derivatives can be synthesized in recombinant culture such as N- or C-terminal fusions or by the use of agents known in the art for their usefulness in cross-linking proteins through reactive side groups. Preferred derivatization sites with cross-linking agents are at free amino groups, carbohydrate moieties, and cysteine residues.

Fusion polypeptides between the receptors and other homologous or heterologous proteins are also provided. Homologous polypeptides may be fusions between different receptors, resulting in, for instance, a hybrid protein exhibiting binding specificity for multiple different cytokine ligands, or a receptor which may have broadened or weakened specificity of substrate effect. Likewise, heterologous fusions may be constructed which would exhibit a combination of properties or activities of the derivative proteins. Typical examples are fusions of a reporter polypeptide, e.g., luciferase, with a segment or domain of a receptor, e.g., a ligand-binding segment, so that the presence or location of a desired ligand may be easily determined. See, e.g., Dull, et al., U.S. Pat. No. 4,859,609, which is hereby incorporated herein by reference. Other gene fusion partners include glutathione-S-transferase (GST), bacterial β-galactosidase, trpE, Protein A, β-lactamase, alpha amylase, alcohol dehydrogenase, and yeast alpha mating factor. See, e.g., Godowski, et al. (1988) *Science* 241:812-816.

The phosphoramidite method described by Beaucage and Carruthers (1981) *Tetra. Letts.* 22:1859-1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence.

Such polypeptides may also have amino acid residues which have been chemically modified by phosphorylation, sulfonation, biotinylation, or the addition or removal of other moieties, particularly those which have molecular shapes similar to phosphate groups. In some embodiments, the modifications will be useful labeling reagents, or serve as purification targets, e.g., affinity ligands.

Fusion proteins will typically be made by either recombinant nucleic acid methods or by synthetic polypeptide methods. Techniques for nucleic acid manipulation and expression are described generally, for example, in Sambrook, et al. (1989) *Molecular Cloning: A Laboratory Manual* (2d ed.), Vols. 1-3, Cold Spring Harbor Laboratory, and Ausubel, et al. (eds. 1987 and periodic supplements) *Current Protocols in Molecular Biology*, Greene/Wiley, New York, which are each incorporated herein by reference. Techniques for synthesis of polypeptides are described, for example, in Merrifield (1963) *J. Amer. Chem. Soc.* 85:2149-2156; Merrifield (1986) *Science* 232: 341-347; and Atherton, et al. (1989) *Solid Phase Peptide Synthesis: A Practical Approach*, IRL Press, Oxford; each of which is incorporated herein by reference. See also Dawson, et al. (1994) *Science* 266:776-779 for methods to make larger polypeptides.

This invention also contemplates the use of derivatives of a DIRS1 other than variations in amino acid sequence or glycosylation. Such derivatives may involve covalent or aggregative association with chemical moieties. These derivatives generally fall into three classes: (1) salts, (2) side chain and terminal residue covalent modifications, and (3) adsorption complexes, for example with cell membranes. Such covalent or aggregative derivatives are useful as immunogens, as reagents in immunoassays, or in purification methods such as for affinity purification of a receptor or other binding molecule, e.g., an antibody. For example, a cytokine ligand can be immobilized by covalent bonding to a solid support such as cyanogen bromide-activated Sepharose, by methods which are well known in the art, or adsorbed onto polyolefin surfaces, with or without glutaraldehyde cross-linking, for use in the assay or purification of an cytokine receptor, antibodies, or other similar molecules. The ligand can also be labeled with a detectable group, for example radioiodinated by the chloramine T procedure, covalently bound to rare earth chelates, or conjugated to another fluorescent moiety for use in diagnostic assays.

An DIRS1 of this invention can be used as an immunogen for the production of antisera or antibodies specific, e.g., capable of distinguishing between other cytokine receptor family members, for the DIRS1 or various fragments thereof. The purified DIRS1 can be used to screen monoclonal antibodies or antigen-binding fragments prepared by immunization with various forms of impure preparations containing the protein. Antibodies can typically be substituted with antigen binding fragments of natural antibodies, e.g., Fab, Fab2, Fv, etc. The purified DIRS1 can also be used as a reagent to detect antibodies generated in response to the presence of elevated levels of expression, or immunological disorders which lead to antibody production to the endogenous receptor. Additionally, DIRS1 fragments may also serve as immunogens to produce the antibodies of the present invention, as described immediately below. For example, this invention contemplates antibodies having binding affinity to or being raised against the amino acid sequences shown in Table 1, fragments thereof, or various homologous peptides. In particular, this invention contemplates antibodies having binding affinity to, or having been raised against, specific fragments which are predicted to be, or actually are, exposed at the exterior protein surface of the native DIRS1.

The blocking of physiological response to the receptor ligands may result from the inhibition of binding of the ligand to the receptor, likely through competitive inhibition. Thus, in vitro assays of the present invention will often use antibodies or antigen binding segments of these antibodies, or fragments attached to solid phase substrates. These assays will also allow for the diagnostic determination of the effects of either ligand binding region mutations and modifications, or other mutations and modifications, e.g., which affect signaling or enzymatic function.

This invention also contemplates the use of competitive drug screening assays, e.g., where neutralizing antibodies to the receptor or fragments compete with a test compound for binding to a ligand or other antibody. In this manner, the neutralizing antibodies or fragments can be used to detect the presence of a polypeptide which shares one or more binding sites to a receptor and can also be used to occupy binding sites on a receptor that might otherwise bind a ligand.

V. Making Nucleic Acids and Protein

DNA which encodes the protein or fragments thereof can be obtained by chemical synthesis, screening cDNA libraries, or by screening genomic libraries prepared from a wide variety of cell lines or tissue samples. Natural sequences can be isolated using standard methods and the sequences provided herein, e.g., in Table 1. Other species counterparts can be identified by hybridization techniques, or by various PCR techniques, combined with or by searching in sequence databases, e.g., GenBank.

This DNA can be expressed in a wide variety of host cells for the synthesis of a full-length receptor or fragments which can in turn, for example, be used to generate polyclonal or monoclonal antibodies; for binding studies; for construction and expression of modified ligand binding or kinase/phosphatase domains; and for structure/function studies. Variants or fragments can be expressed in host cells that are transformed or transfected with appropriate expression vectors. These molecules can be substantially free of protein or cellular contaminants, other than those derived from the recombinant host, and therefore are particularly useful in pharmaceutical compositions when combined with a pharmaceutically acceptable carrier and/or diluent. The protein, or portions thereof, may be expressed as fusions with other proteins.

Expression vectors are typically self-replicating DNA or RNA constructs containing the desired receptor gene or its fragments, usually operably linked to suitable genetic control elements that are recognized in a suitable host cell. These control elements are capable of effecting expression within a suitable host. The specific type of control elements necessary to effect expression will depend upon the eventual host cell used. Generally, the genetic control elements can include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also usually contain an origin of replication that allows the vector to replicate independently of the host cell.

The vectors of this invention include those which contain DNA which encodes a protein, as described, or a fragment thereof encoding a biologically active equivalent polypeptide. The DNA can be under the control of a viral promoter and can encode a selection marker. This invention further contemplates use of such expression vectors which are capable of expressing eukaryotic cDNA coding for such a protein in a prokaryotic or eukaryotic host, where the vector is compatible with the host and where the eukaryotic cDNA coding for the receptor is inserted into the vector such that growth of the host containing the vector expresses the cDNA in question. Usually, expression vectors are designed for stable replication in their host cells or for amplification to greatly increase the total number of copies of the desirable gene per cell. It is not always necessary to require that an expression vector replicate in a host cell, e.g., it is possible to effect transient expression of the protein or its fragments in various hosts using vectors that do not contain a replication origin that is recognized by the host cell. It is also possible to use vectors that cause integration of the protein encoding portion or its fragments into the host DNA by recombination.

Vectors, as used herein, comprise plasmids, viruses, bacteriophage, integratable DNA fragments, and other vehicles which enable the integration of DNA fragments into the genome of the host. Expression vectors are specialized vectors which contain genetic control elements that effect expression of operably linked genes. Plasmids are the most commonly used form of vector but all other forms of vectors which serve an equivalent function and which are, or become, known in the art are suitable for use herein. See, e.g., Pouwels, et al. (1985 and Supplements) *Cloning Vectors: A Laboratory Manual*, Elsevier, N.Y., and Rodriguez, et al. (eds. 1988) *Vectors: A Survey of Molecular Cloning Vectors and Their Uses*, Buttersworth, Boston, which are incorporated herein by reference.

Transformed cells are cells, preferably mammalian, that have been transformed or transfected with receptor vectors constructed using recombinant DNA techniques. Transformed host cells usually express the desired protein or its fragments, but for purposes of cloning, amplifying, and manipulating its DNA, do not need to express the subject protein. This invention further contemplates culturing transformed cells in a nutrient medium, thus permitting the receptor to accumulate in the cell membrane. The protein can be recovered, either from the culture or, in certain instances, from the culture medium.

For purposes of this invention, nucleic sequences are operably linked when they are functionally related to each other. For example, DNA for a presequence or secretory leader is operably linked to a polypeptide if it is expressed as a preprotein or participates in directing the polypeptide to the cell membrane or in secretion of the polypeptide. A promoter is operably linked to a coding sequence if it controls the transcription of the polypeptide; a ribosome binding site is operably linked to a coding sequence if it is positioned to permit translation. Usually, operably linked means contiguous and in reading frame, however, certain genetic elements such as repressor genes are not contiguously linked but still bind to operator sequences that in turn control expression.

Suitable host cells include prokaryotes, lower eukaryotes, and higher eukaryotes. Prokaryotes include both gram negative and gram positive organisms, e.g., *E. coli* and *B. subtilis*. Lower eukaryotes include yeasts, e.g., *S. cerevisiae* and *Pichia*, and species of the genus *Dictyostelium*. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or many of its derivatives. Vectors that can be used to express the receptor or its fragments include, but are not limited to, such vectors as those containing the lac promoter (pUC-series); trp promoter (pBR322-trp); Ipp promoter (the pIN-series); lambda-pP or pR promoters (pOTS); or hybrid promoters such as ptac (pDR540). See Brosius, et al. (1988) "Expression Vectors Employing Lambda-, trp-, lac-, and Ipp-derived Promoters", in *Vectors: A Survey of Molecular Cloning Vectors and Their Uses*, (eds. Rodriguez and Denhardt), Buttersworth, Boston, Chapter 10, pp. 205-236, which is incorporated herein by reference.

Lower eukaryotes, e.g., yeasts and *Dictyostelium*, may be transformed with DIRS1 sequence containing vectors. For purposes of this invention, the most common lower eukaryotic host is the baker's yeast, *Saccharomyces cerevisiae*. It will be used to generically represent lower eukaryotes although a number of other strains and species are also available. Yeast vectors typically consist of a replication origin (unless of the integrating type), a selection gene, a promoter, DNA encoding the receptor or its fragments, and sequences for translation termination, polyadenylation, and transcription termination. Suitable expression vectors for yeast include such constitutive promoters as 3-phosphoglycerate kinase and various other glycolytic enzyme gene promoters or such inducible promoters as the alcohol dehydrogenase 2 promoter or metallothionine promoter. Suitable vectors include derivatives of the following types: self-replicating low copy number (such as the YRp-series), self-replicating high copy number (such as the YEp-series); integrating types (such as the YIp-series), or mini-chromosomes (such as the YCp-series).

Higher eukaryotic tissue culture cells are normally the preferred host cells for expression of the functionally active interleukin protein. In principle, many higher eukaryotic tissue culture cell lines are workable, e.g., insect baculovirus expression systems, whether from an invertebrate or vertebrate source. However, mammalian cells are preferred. Transformation or transfection and propagation of such cells has become a routine procedure. Examples of useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (if genomic DNA is used), a polyadenylation site, and a transcription termination site. These vectors also usually contain a selection gene or amplification gene. Suitable expression vectors may be plasmids, viruses, or retroviruses carrying promoters derived, e.g., from such sources as from adenovirus, SV40, parvoviruses, vaccinia virus, or cytomegalovirus. Representative examples of suitable expression vectors include pcDNA1; pCD, see Okayama, et al. (1985) *Mol. Cell. Biol.* 5:1136-1142; pMC1neo PolyA, see Thomas, et al. (1987) *Cell* 51:503-512; and a baculovirus vector such as pAC 373 or pAC 610.

For secreted proteins, an open reading frame usually encodes a polypeptide that consists of a mature or secreted product covalently linked at its N-terminus to a signal peptide. The signal peptide is cleaved prior to secretion of the mature, or active, polypeptide. The cleavage site can be predicted with a high degree of accuracy from empirical rules, e.g., von-Heijne (1986) *Nucleic Acids Research* 14:4683-4690 and Nielsen, et al. (1997) *Protein Eng.* 10:1-12, and the precise amino acid composition of the signal peptide often does not appear to be critical to its function, e.g., Randall, et al. (1989) *Science* 243:1156-1159; Kaiser et al. (1987) *Science* 235:312-317.

It will often be desired to express these polypeptides in a system which provides a specific or defined glycosylation pattern. In this case, the usual pattern will be that provided naturally by the expression system. However, the pattern will be modifiable by exposing the polypeptide, e.g., an unglycosylated form, to appropriate glycosylating proteins introduced into a heterologous expression system. For example, the receptor gene may be co-transformed with one or more genes encoding mammalian or other glycosylating enzymes. Using this approach, certain mammalian glycosylation patterns will be achievable in prokaryote or other cells.

The source of DIRS1 can be a eukaryotic or prokaryotic host expressing recombinant DIRS1, such as is described above. The source can also be a cell line such as mouse Swiss 3T3 fibroblasts, but other mammalian cell lines are also contemplated by this invention, with the preferred cell line being from the human species.

Now that the sequences are known, the primate DIRS1, fragments, or derivatives thereof can be prepared by conventional processes for synthesizing peptides. These include processes such as are described in Stewart and Young (1984) *Solid Phase Peptide Synthesis*, Pierce Chemical Co., Rockford, Ill.; Bodanszky and Bodanszky (1984) *The Practice of Peptide Synthesis*, Springer-Verlag, New York; and Bodanszky (1984) *The Principles of Peptide Synthesis*, Springer-Verlag, New York; all of each which are incorporated herein by reference. For example, an azide process, an acid chloride process, an acid anhydride process, a mixed anhydride process, an active ester process (for example, p-nitrophenyl ester, N-hydroxysuccinimide ester, or cyanomethyl ester), a carbodiimidazole process, an oxidative-reductive process, or a dicyclohexylcarbodiimide (DCCD)/additive process can be used. Solid phase and solution phase syntheses are both applicable to the foregoing processes. Similar techniques can be used with partial DIRS1 sequences.

The DIRS1 proteins, fragments, or derivatives are suitably prepared in accordance with the above processes as typically employed in peptide synthesis, generally either by a so-called stepwise process which comprises condensing an amino acid to the terminal amino acid, one by one in sequence, or by coupling peptide fragments to the terminal amino acid. Amino groups that are not being used in the coupling reaction typically must be protected to prevent coupling at an incorrect location.

If a solid phase synthesis is adopted, the C-terminal amino acid is bound to an insoluble carrier or support through its carboxyl group. The insoluble carrier is not particularly limited as long as it has a binding capability to a reactive carboxyl group. Examples of such insoluble carriers include halomethyl resins, such as chloromethyl resin or bromomethyl resin, hydroxymethyl resins, phenol resins, tert-alkyloxycarbonylhydrazidated resins, and the like.

An amino group-protected amino acid is bound in sequence through condensation of its activated carboxyl group and the reactive amino group of the previously formed peptide or chain, to synthesize the peptide step by step. After synthesizing the complete sequence, the peptide is split off from the insoluble carrier to produce the peptide. This solid-phase approach is generally described by Merrifield, et al. (1963) in *J. Am. Chem. Soc.* 85:2149-2156, which is incorporated herein by reference.

The prepared protein and fragments thereof can be isolated and purified from the reaction mixture by means of peptide separation, for example, by extraction, precipitation, electrophoresis, various forms of chromatography, and the like. The receptors of this invention can be obtained in varying degrees of purity depending upon desired uses. Purification can be accomplished by use of the protein purification techniques disclosed herein, see below, or by the use of the antibodies herein described in methods of immunoabsorbant affinity chromatography. This immunoabsorbant affinity chromatography is carried out by first linking the antibodies to a solid support and then contacting the linked antibodies with solubilized lysates of appropriate cells, lysates of other cells expressing the receptor, or lysates or supernatants of cells producing the protein as a result of DNA techniques, see below.

Generally, the purified protein will be at least about 40% pure, ordinarily at least about 50% pure, usually at least about 60% pure, typically at least about 70% pure, more typically at least about 80% pure, preferable at least about 90% pure and more preferably at least about 95% pure, and in particular embodiments, 97%-99% or more. Purity will usually be on a weight basis, but can also be on a molar basis. Different assays will be applied as appropriate.

VI. Antibodies

Antibodies can be raised to the various mammalian, e.g., primate DIRS1 proteins and fragments thereof, both in naturally occurring native forms and in their recombinant forms, the difference being that antibodies to the active receptor are more likely to recognize epitopes which are only present in the native conformations. Denatured antigen detection can also be useful in, e.g., Western analysis. Anti-idiotypic antibodies are also contemplated, which would be useful as agonists or antagonists of a natural receptor or an antibody.

Antibodies, including binding fragments and single chain versions, against predetermined fragments of the protein can be raised by immunization of animals with conjugates of the fragments with immunogenic proteins. Monoclonal antibodies are prepared from cells secreting the desired antibody. These antibodies can be screened for binding to normal or defective protein, or screened for agonistic or antagonistic activity. These monoclonal antibodies will usually bind with at least a $K_D$ of about 1 mM, more usually at least about 300 µM, typically at least about 100 µM, more typically at least about 30 µM, preferably at least about 10 µM, and more preferably at least about 3 µM or better.

The antibodies, including antigen binding fragments, of this invention can have significant diagnostic or therapeutic value. They can be potent antagonists that bind to the receptor and inhibit binding to ligand or inhibit the ability of the receptor to elicit a biological response, e.g., act on its substrate. They also can be useful as non-neutralizing antibodies and can be coupled to toxins or radionuclides to bind producing cells, or cells localized to the source of the interleukin. Further, these antibodies can be conjugated to drugs or other therapeutic agents, either directly or indirectly by means of a linker.

The antibodies of this invention can also be useful in diagnostic applications. As capture or non-neutralizing antibodies, they might bind to the receptor without inhibiting ligand or substrate binding. As neutralizing antibodies, they can be useful in competitive binding assays. They will also be useful in detecting or quantifying ligand. They may be used as reagents for Western blot analysis, or for immunoprecipitation or immunopurification of the respective protein.

Protein fragments may be joined to other materials, particularly polypeptides, as fused or covalently joined polypeptides to be used as immunogens. Mammalian cytokine receptors and fragments may be fused or covalently linked to a variety of immunogens, such as keyhole limpet hemocyanin, bovine serum albumin, tetanus toxoid, etc. See *Microbiology*, Hoeber Medical Division, Harper and Row, 1969; Landsteiner (1962) *Specificity of Serological Reactions*, Dover Publications, New York; and Williams, et al. (1967) *Methods in Immunology and Immunochemistry*, Vol. 1, Academic Press, New York; each of which are incorporated herein by reference, for descriptions of methods of preparing polyclonal antisera. A typical method involves hyperimmunization of an animal with an antigen. The blood of the animal is then collected shortly after the repeated immunizations and the gamma globulin is isolated.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) *Basic and Clinical Immunology* (4th ed.), Lange Medical Publications, Los Altos, Calif., and references cited therein; Harlow and Lane (1988) *Antibodies: A Laboratory Manual*, CSH Press; Goding (1986) *Monoclonal Antibodies: Principles and Practice* (2d ed.) Academic Press, New York; and particularly in Kohler and Milstein (1975) in *Nature* 256: 495-497, which discusses one method of generating monoclonal antibodies. Each of these references is incorporated herein by reference. Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve in vitro exposure of lymphocytes to the antigenic polypeptides or alternatively to selection of libraries of antibodies in phage or similar vectors. See, Huse, et al. (1989) "Generation of a Large Combinatorial Library of the Immunoglobulin Repertoire in Phage Lambda," *Science* 246:1275-1281; and Ward, et al. (1989) *Nature* 341:544-546, each of which is hereby incorporated herein by reference. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant or chimeric immunoglobulins may be produced, see Cabilly, U.S. Pat. No. 4,816,567; or made in transgenic mice, see, e.g., Mendez, et al. (1997) *Nature Genetics* 15:146-156. These references are incorporated herein by reference.

The antibodies of this invention can also be used for affinity chromatography in isolating the DIRS1 proteins or peptides. Columns can be prepared where the antibodies are linked to a solid support, e.g., particles, such as agarose, Sephadex, or the like, where a cell lysate may be passed through the column, the column washed, followed by increasing concentrations of a mild denaturant, whereby the purified protein will be released. The protein may be used to purify antibody. Conversely, the antibodies may be immunoselected or immunodepleted to provide binding compositions of defined specificities.

The antibodies may also be used to screen expression libraries for particular expression products. Usually the antibodies used in such a procedure will be labeled with a moiety allowing easy detection of presence of antigen by antibody binding.

Antibodies raised against a cytokine receptor will also be used to raise anti-idiotypic antibodies. These will be useful in detecting or diagnosing various immunological conditions related to expression of the protein or cells which express the protein. They also will be useful as agonists or antagonists of the ligand, which may be competitive inhibitors or substitutes for naturally occurring ligands.

A cytokine receptor protein that specifically binds to or that is specifically immunoreactive with an antibody generated against a defined immunogen, such as an immunogen consisting of the amino acid sequence of SEQ ID NO: 2, is typically determined in an immunoassay. The immunoassay typically uses a polyclonal antiserum which was raised, e.g., to a protein of SEQ ID NO: 2. This antiserum is selected to have low crossreactivity against other cytokine receptor family members, e.g., IL-12 receptor beta or gp130, preferably from the same species, and any such crossreactivity is removed by immunoabsorption prior to use in the immunoassay.

In order to produce antisera for use in an immunoassay, the protein, e.g., of SEQ ID NO: 2, is isolated as described herein. For example, recombinant protein may be produced in a mammalian cell line. An appropriate host, e.g., an inbred strain of mice such as Balb/c, is immunized with the selected protein, typically using a standard adjuvant, such as Freund's adjuvant, and a standard mouse immunization protocol (see Harlow and Lane, supra). Alternatively, a synthetic peptide derived from the sequences disclosed herein and conjugated to a carrier protein can be used an immunogen. Polyclonal sera are collected and titered against the immunogen protein in an immunoassay, e.g., a solid phase immunoassay with the immunogen immobilized on a solid support. Polyclonal antisera with a titer of $10^4$ or greater are selected and tested for their cross reactivity against other cytokine receptor family members, e.g., IL-12 receptor beta and/or gp130, using a competitive binding immunoassay such as the one described in Harlow and Lane, supra, at pages 570-573. Preferably at least two cytokine receptor family members are used in this determination. These cytokine receptor family members can be produced as recombinant proteins and isolated using standard molecular biology and protein chemistry techniques as described herein.

Immunoassays in the competitive binding format can be used for the crossreactivity determinations. For example, the protein of SEQ ID NO: 2 can be immobilized to a solid support. Proteins added to the assay compete with the binding of the antisera to the immobilized antigen. The ability of the above proteins to compete with the binding of the antisera to the immobilized protein is compared to the proteins of IL-12 receptor beta or gp130. The percent crossreactivity for the above proteins is calculated, using standard calculations. Those antisera with less than 10% crossreactivity with each of the proteins listed above are selected and pooled. The cross-reacting antibodies are then removed from the pooled antisera by immunoabsorption with the above-listed proteins.

The immunoabsorbed and pooled antisera are then used in a competitive binding immunoassay as described above to compare a second protein to the immunogen protein (e.g., the DIRS1 like protein of SEQ ID NO: 2). In order to make this comparison, the two proteins are each assayed at a wide range of concentrations and the amount of each protein required to inhibit 50% of the binding of the antisera to the immobilized protein is determined. If the amount of the second protein required is less than twice the amount of the protein of the selected protein or proteins that is required, then the second protein is said to specifically bind to an antibody generated to the immunogen.

It is understood that these cytokine receptor proteins are members of a family of homologous proteins that comprise at least 6 so far identified genes. For a particular gene product, such as the DIRS1, the term refers not only to the amino acid sequences disclosed herein, but also to other proteins that are allelic, non-allelic, or species variants. It is also understood that the terms include nonnatural mutations introduced by deliberate mutation using conventional recombinant technology such as single site mutation, or by excising short sections of DNA encoding the respective proteins, or by substituting new amino acids, or adding new amino acids. Such minor alterations typically will substantially maintain the immunoidentity of the original molecule and/or its biological activity. Thus, these alterations include proteins that are specifically immunoreactive with a designated naturally occurring DIRS1 protein. The biological properties of the altered proteins can be determined by expressing the protein in an appropriate cell line and measuring the appropriate effect, e.g., upon transfected lymphocytes. Particular protein modifications considered minor would include conservative substitution of amino acids with similar chemical properties, as described above for the cytokine receptor family as a whole. By aligning a protein optimally with the protein of the cytokine receptors and by using the conventional immunoassays described herein to determine immunoidentity, one can determine the protein compositions of the invention.

VII. Kits and Quantitation

Both naturally occurring and recombinant forms of the cytokine receptor like molecules of this invention are particularly useful in kits and assay methods. For example, these methods would also be applied to screening for binding activity, e.g., ligands for these proteins. Several methods of automating assays have been developed in recent years so as to permit screening of tens of thousands of compounds per year. See, e.g., a BIOMEK automated workstation, Beckman Instruments, Palo Alto, Calif., and Fodor, et al. (1991) *Science* 251:767-773, which is incorporated herein by reference. The latter describes means for testing binding by a plurality of defined polymers synthesized on a solid substrate. The development of suitable assays to screen for a ligand or agonist/antagonist homologous proteins can be greatly facilitated by the availability of large amounts of purified, soluble cytokine receptors in an active state such as is provided by this invention.

Purified DIRS1 can be coated directly onto plates for use in the aforementioned ligand screening techniques. However, non-neutralizing antibodies to these proteins can be used as capture antibodies to immobilize the respective receptor on the solid phase, useful, e.g., in diagnostic uses.

This invention also contemplates use of DIRS1, fragments thereof, peptides, and their fusion products in a variety of diagnostic kits and methods for detecting the presence of the protein or its ligand. Alternatively, or additionally, antibodies against the molecules may be incorporated into the kits and methods. Typically the kit will have a compartment containing either a DIRS1 peptide or gene segment or a reagent which recognizes one or the other. Typically, recognition reagents, in the case of peptide, would be a receptor or antibody, or in the case of a gene segment, would usually be a hybridization probe.

A preferred kit for determining the concentration of DIRS1 in a sample would typically comprise a labeled compound, e.g., ligand or antibody, having known binding affinity for DIRS1, a source of DIRS1 (naturally occurring or recombinant) as a positive control, and a means for separating the bound from free labeled compound, for example a solid phase for immobilizing the DIRS1 in the test sample. Compartments containing reagents, and instructions, will normally be provided.

Antibodies, including antigen binding fragments, specific for mammalian DIRS1 or a peptide fragment, or receptor fragments are useful in diagnostic applications to detect the presence of elevated levels of ligand and/or its fragments. Diagnostic assays may be homogeneous (without a separation step between free reagent and antibody-antigen complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA) and the like. For example, unlabeled antibodies can be employed by using a second antibody which is labeled and which recognizes the antibody to a cytokine receptor or to a particular fragment thereof. These assays have also been extensively discussed in the literature. See, e.g., Harlow and Lane (1988) *Antibodies: A Laboratory Manual*, CSH., and Coligan (ed. 1991 and periodic supplements) *Current Protocols In Immunology* Greene/Wiley, New York.

Anti-idiotypic antibodies may have similar use to serve as agonists or antagonists of cytokine receptors. These should be useful as therapeutic reagents under appropriate circumstances.

Frequently, the reagents for diagnostic assays are supplied in kits, so as to optimize the sensitivity of the assay. For the subject invention, depending upon the nature of the assay, the protocol, and the label, either labeled or unlabeled antibody, or labeled ligand is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent, and will contain instructions for proper use and disposal of reagents. Desirably, the reagents are provided as a dry lyophilized powder, where the reagents may be reconstituted in an aqueous medium having appropriate concentrations for performing the assay.

The aforementioned constituents of the diagnostic assays may be used without modification or may be modified in a variety of ways. For example, labeling may be achieved by covalently or non-covalently joining a moiety which directly or indirectly provides a detectable signal. In many of these assays, a test compound, cytokine receptor, or antibodies thereto can be labeled either directly or indirectly. Possibilities for direct labeling include label groups: radiolabels such as $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Both of the patents are incorporated herein by reference. Possibilities for indirect labeling include biotinylation of one constituent followed by binding to avidin coupled to one of the above label groups.

There are also numerous methods of separating the bound from the free ligand, or alternatively the bound from the free test compound. The cytokine receptor can be immobilized on various matrixes followed by washing. Suitable matrices include plastic such as an ELISA plate, filters, and beads. Methods of immobilizing the receptor to a matrix include, without limitation, direct adhesion to plastic, use of a capture antibody, chemical coupling, and biotin-avidin. The last step in this approach involves the precipitation of antibody/antigen complex by any of several methods including those utilizing, e.g., an organic solvent such as polyethylene glycol or a salt such as ammonium sulfate. Other suitable separation techniques include, without limitation, the fluorescein antibody magnetizable particle method described in Rattle, et al. (1984) *Clin. Chem.* 30(9):1457-1461, and the double antibody magnetic particle separation as described in U.S. Pat. No. 4,659,678, each of which is incorporated herein by reference.

The methods for linking protein or fragments to various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of an cytokine receptor. These sequences can be used as probes for detecting levels of the respective cytokine receptor in patients suspected of having an immunological disorder. The preparation of both RNA and DNA nucleotide sequences, the labeling of the sequences, and the preferred size of the sequences has received ample description and discussion in the literature. Normally an oligonucleotide probe should have at least about 14 nucleotides, usually at least about 18 nucleotides, and the polynucleotide probes may be up to several kilobases. Various labels may be employed, most commonly radionuclides, particularly $^{32}$P. However, other techniques may also be employed, such as using biotin modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed which can recognize specific duplexes, including DNA duplexes, RNA duplexes, DNA-RNA hybrid duplexes, or DNA-protein duplexes. The antibodies in turn may be labeled and the assay carried out where the duplex is bound to a surface, so that upon the formation of duplex on the surface, the presence of antibody bound to the duplex can be detected. The use of probes to the novel anti-sense RNA may be carried out in conventional techniques such as nucleic acid hybridization, plus and minus screening, recombinational probing, hybrid released translation (HRT), and hybrid arrested translation (HART). This also includes amplification techniques such as polymerase chain reaction (PCR).

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet, et al. (1989) *Progress in Growth Factor Res.* 1:89-97.

VIII. Therapeutic Utility

This invention provides reagents with significant therapeutic value. See, e.g., Levitzki (1996) *Curr. Opin. Cell Biol.* 8:239-244. The cytokine receptors (naturally occurring or recombinant), fragments thereof, mutein receptors, and antibodies, along with compounds identified as having binding affinity to the receptors or antibodies, should be useful in the treatment of conditions exhibiting abnormal expression of the receptors of their ligands. Such abnormality will typically be manifested by immunological disorders. Additionally, this invention should provide therapeutic value in various diseases or disorders associated with abnormal expression or abnormal triggering of response to the ligand. For example, the IL-1 ligands have been suggested to be involved in morphologic development, e.g., dorso-ventral polarity determination, and immune responses, particularly the primitive innate responses. See, e.g., Sun, et al. (1991) *Eur. J. Biochem.* 196:247-254; and Hultmark (1994) *Nature* 367:116-117.

Recombinant cytokine receptors, muteins, agonist or antagonist antibodies thereto, or antibodies can be purified and then administered to a patient. These reagents can be combined for therapeutic use with additional active ingredients, e.g., in conventional pharmaceutically acceptable carriers or diluents, along with physiologically innocuous stabilizers and excipients. These combinations can be sterile, e.g., filtered, and placed into dosage forms as by lyophilization in dosage vials or storage in stabilized aqueous preparations. This invention also contemplates use of antibodies or binding fragments thereof which are not complement binding.

Ligand screening using cytokine receptor or fragments thereof can be performed to identify molecules having binding affinity to the receptors. Subsequent biological assays can then be utilized to determine if a putative ligand can provide competitive binding, which can block intrinsic stimulating activity. Receptor fragments can be used as a blocker or antagonist in that it blocks the activity of ligand. Likewise, a compound having intrinsic stimulating activity can activate the receptor and is thus an agonist in that it simulates the activity of ligand, e.g., inducing signaling. This invention further contemplates the therapeutic use of antibodies to cytokine receptors as antagonists.

The quantities of reagents necessary for effective therapy will depend upon many different factors, including means of administration, target site, reagent physiological life, pharmacological life, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds. 1990) *Goodman and Gilman's: The Pharmacological Bases of Therapeutics*, 8th Ed., Pergamon Press; and *Remington's Pharmaceutical Sciences*, 17th ed. (1990), Mack Publishing Co., Easton, Pa.; each of which is hereby incorporated herein by reference. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index*, Merck & Co., Rahway, N.J. Because of the likely high affinity binding, or turnover numbers, between a putative ligand and its receptors, low dosages of these reagents would be initially expected to be effective. And the signaling pathway suggests extremely low amounts of ligand may have effect. Thus, dosage ranges would ordinarily be expected to be in amounts lower than 1 mM concentrations, typically less than about 10 µM concentrations, usually less than about 100 nM, preferably less than about 10 pM (picomolar), and most preferably less than about 1 fM (femtomolar), with an appropriate carrier. Slow release formulations, or slow release apparatus will often be utilized for continuous administration.

Cytokine receptors, fragments thereof, and antibodies or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in many conventional dosage formulations. While it is possible for the active ingredient to be administered alone, it is preferable to present it as a pharmaceutical formulation. Formulations comprise at least one active ingredient, as defined above, together with one or more acceptable carriers thereof. Each carrier must be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by methods well known in the art of pharmacy. See, e.g., Gilman, et al. (eds. 1990) *Goodman and Gilman's: The Pharmacological Bases of Therapeutics*, 8th Ed., Pergamon Press; and *Remington's Pharmaceutical Sciences*, 17th ed. (1990), Mack Publishing Co., Easton, Pa.; Avis, et al. (eds. 1993) *Pharmaceutical Dosage Forms Parenteral Medications* Dekker, NY; Lieberman, et al. (eds. 1990) *Pharmaceutical Dosage Forms: Tablets* Dekker, NY; and Lieberman, et al. (eds. 1990) *Pharmaceutical Dosage Forms Disperse Systems* Dekker, NY. The therapy of this invention may be combined with or used in association with other therapeutic agents, particularly agonists or antagonists of other cytokine receptor family members.

IX. Screening

Drug screening using DIRS1 or fragments thereof can be performed to identify compounds having binding affinity to the receptor subunit, including isolation of associated components. Subsequent biological assays can then be utilized to determine if the compound has intrinsic stimulating activity and is therefore a blocker or antagonist in that it blocks the activity of the ligand. Likewise, a compound having intrinsic stimulating activity can activate the receptor and is thus an agonist in that it simulates the activity of a cytokine ligand. This invention further contemplates the therapeutic use of antibodies to the receptor as cytokine agonists or antagonists.

One method of drug screening utilizes eukaryotic or prokaryotic host cells which are stably transformed with recombinant DNA molecules expressing the DIRS1. Cells may be isolated which express a receptor in isolation from other functional receptors. Such cells, either in viable or fixed form, can be used for standard ligand/receptor binding assays. See also, Parce, et al. (1989) *Science* 246:243-247; and Owicki, et al. (1990) *Proc. Nat'l Acad. Sci. USA* 87:4007-4011, which describe sensitive methods to detect cellular responses. Competitive assays are particularly useful, where the cells (source of putative ligand) are contacted and incubated with a labeled receptor or antibody having known binding affinity to the ligand, such as $^{125}$I-antibody, and a test sample whose binding affinity to the binding composition is being measured. The bound and free labeled binding compositions are then separated to assess the degree of ligand binding. The amount of test compound bound is inversely proportional to the amount of labeled receptor binding to the known source. Any one of numerous techniques can be used to separate bound from free ligand to assess the degree of ligand binding. This separation step could typically involve a procedure such as adhesion to filters followed by washing, adhesion to plastic followed by washing, or centrifugation of the cell membranes. Viable cells could also be used to screen for the effects of drugs on cytokine mediated functions, e.g., second messenger levels, i.e., $Ca^{++}$; cell proliferation; inositol phosphate pool changes; and others. Some detection methods allow for elimination of a separation step, e.g., a proximity sensitive detection system. Calcium sensitive dyes will be useful for detecting $Ca^{++}$ levels, with a fluorimeter or a fluorescence cell sorting apparatus.

X. Ligands

The descriptions of the DIRS1 herein provide means to identify ligands, as described above. Such ligand should bind specifically to the respective receptor with reasonably high affinity. Various constructs are made available which allow either labeling of the receptor to detect its ligand. For example, directly labeling cytokine receptor, fusing onto it markers for secondary labeling, e.g., FLAG or other epitope tags, etc., will allow detection of receptor. This can be histological, as an affinity method for biochemical purification, or labeling or selection in an expression cloning approach. A two-hybrid selection system may also be applied making appropriate constructs with the available cytokine receptor sequences. See, e.g., Fields and Song (1989) *Nature* 340:245-246.

Generally, descriptions of cytokine receptors will be analogously applicable to individual specific embodiments directed to DIRS1 reagents and compositions.

The broad scope of this invention is best understood with reference to the following examples, which are not intended to limit the inventions to the specific embodiments.

EXAMPLES

I. General Methods

Some of the standard methods are described or referenced, e.g., in Maniatis, et al. (1982) *Molecular Cloning, A Laboratory Manual*, Cold Spring Harbor Laboratory, Cold Spring Harbor Press; Sambrook, et al. (1989) *Molecular Cloning: A Laboratory Manual*, (2d ed.), vols. 1-3, CSH Press, NY; Ausubel, et al., *Biology*, Greene Publishing Associates, Brooklyn, N.Y.; or Ausubel, et al. (1987 and Supplements) *Current Protocols in Molecular Biology*, Greene/Wiley, New York. Methods for protein purification include such methods as ammonium sulfate precipitation, column chromatography, electrophoresis, centrifugation, crystallization, and others. See, e.g., Ausubel, et al. (1987 and periodic supplements); Coligan, et al. (ed. 1996) and periodic supplements, *Current Protocols In Protein Science* Greene/Wiley, New York; Deutscher (1990) "Guide to Protein Purification" in *Methods in Enzymology*, vol. 182, and other volumes in this series; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See, e.g., Hochuli (1989) *Chemische Industrie* 12:69-70; Hochuli (1990) "Purification of Recombinant Proteins with Metal Chelate Absorbent" in Setlow (ed.) *Genetic Engineering, Principle and Methods* 12:87-98, Plenum Press, N.Y.; and Crowe, et al. (1992) *QIAexpress: The High Level Expression & Protein Purification System* QUIAGEN, Inc., Chatsworth, Calif.

Computer sequence analysis is performed, e.g., using available software programs, including those from the GCG (U. Wisconsin) and GenBank sources. Public sequence databases were also used, e.g., from GenBank and others.

Many techniques applicable to IL-10 or IL-12 receptors may be applied to the DIRS1, as described, e.g., in U.S. Ser. No. 08/110,683 (IL-10 receptor), which is incorporated herein by reference.

II. Computational Analysis

Human sequences related to cytokine receptors were identified from genomic sequence database using, e.g., the BLAST server (Altschul, et al. (1994) *Nature Genet.* 6:119-129). Standard analysis programs may be used to evaluate structure, e.g., PHD (Rost and Sander (1994) *Proteins* 19:55-72) and DSC (King and Sternberg (1996) *Protein Sci.* 5:2298-2310). Standard comparison software includes, e.g., Altschul, et al. (1990) *J. Mol. Biol.* 215:403-10; Waterman (1995) *Introduction to Computational Biology: Maps, Sequences, and Genomes* Chapman & Hall; Lander and Waterman (eds. 1995) *Calculating the Secrets of Life: Applications of the Mathematical Sciences in Molecular Biology* National Academy Press; and Speed and Waterman (eds. 1996) *Genetic Mapping and DNA Sequencing* (Ima Volumes in Mathematics and Its Applications, Vol 81) Springer Verlag.

III. Cloning of Full-Length DIRS cDNAs; Chromosomal Localization

PCR primers derived from the DIRS sequences are used to probe a human cDNA library. Full length cDNAs for primate, rodent, or other species DIRS1 are cloned, e.g., by DNA hybridization screening of λgt10 phage. PCR reactions are conducted using *T. aquaticus* Taqplus DNA polymerase (Stratagene) under appropriate conditions.

Chromosome spreads are prepared. In situ hybridization is performed on chromosome preparations obtained from phytohemagglutinin-stimulated human lymphocytes cultured for 72 h. 5-bromodeoxyuridine was added for the final seven hours of culture (60 µg/ml of medium), to ensure a posthybridization chromosomal banding of good quality.

A PCR fragment, amplified with the help of primers, is cloned into an appropriate vector. The vector is labeled by nick-translation with $^3$H. The radiolabeled probe is hybridized to metaphase spreads at final concentration of 200 ng/ml of hybridization solution as described in Mattei, et al. (1985) *Hum. Genet.* 69:327-331.

After coating with nuclear track emulsion (KODAK NTB$_2$), slides are exposed. To avoid any slipping of silver grains during the banding procedure, chromosome spreads are first stained with buffered Giemsa solution and metaphase photographed. R-banding is then performed by the fluorochrome-photolysis-Giemsa (FPG) method and metaphases rephotographed before analysis. Alternatively, mapped sequence tags may be searched in a database.

Similar appropriate methods are used for other species.

IV. Localization of DIRS1 or DIRS2 mRNA

Human multiple tissue (Cat# 1, 2) and cancer cell line blots (Cat# 7757-1), containing approximately 2 µg of poly(A)$^+$ RNA per lane, are purchased from Clontech (Palo Alto, Calif.). Probes are radiolabeled with [α-$^{32}$P] dATP, e.g., using the Amersham Rediprime random primer labeling kit (RPN1633). Prehybridization and hybridizations are performed at 65° C. in 0.5 M Na$_2$HPO$_4$, 7% SDS, 0.5 M EDTA (pH 8.0). High stringency washes are conducted, e.g., at 65° C. with two initial washes in 2×SSC, 0.1% SDS for 40 min followed by a subsequent wash in 0.1×SSC, 0.1% SDS for 20 min. Membranes are then exposed at −70° C. to X-Ray film (Kodak) in the presence of intensifying screens. More detailed studies by cDNA library Southerns are performed with selected human DIRS1 clones to examine their expression in hemopoietic or other cell subsets.

Alternatively, two appropriate primers are selected from Table 1 or 2. RT-PCR is used on an appropriate mRNA sample selected for the presence of message to produce a cDNA, e.g., a sample which expresses the gene.

Full length clones may be isolated by hybridization of cDNA libraries from appropriate tissues pre-selected by PCR signal. Northern blots can be performed.

Message for genes encoding DIRS1 will be assayed by appropriate technology, e.g., PCR, immunoassay, hybridization, or otherwise. Tissue and organ cDNA preparations are available, e.g., from Clontech, Mountain View, Calif. Identification of sources of natural expression are useful, as described. And the identification of functional receptor subunit pairings will allow for prediction of what cells express the combination of receptor subunits which will result in a physiological responsiveness to each of the cytokine ligands.

For mouse distribution, e.g., Southern Analysis can be performed: DNA (5 µg) from a primary amplified cDNA library was digested with appropriate restriction enzymes to release the inserts, run on a 1% agarose gel and transferred to a nylon membrane (Schleicher and Schuell, Keene, N.H.).

Samples for mouse mRNA isolation may include: resting mouse fibroblastic L cell line (C200); Braf:ER (Braf fusion to estrogen receptor) transfected cells, control (C201); T cells, TH1 polarized (Mel14 bright, CD4+ cells from spleen, polarized for 7 days with IFN-γ and anti IL-4; T200); T cells, TH2 polarized (Mel14 bright, CD4+ cells from spleen, polarized for 7 days with IL-4 and anti-IFN-γ; T201); T cells, highly TH1 polarized (see Openshaw, et al. (1995) *J. Exp. Med.* 182:1357-1367; activated with anti-CD3 for 2, 6, 16 h pooled; T202); T cells, highly TH2 polarized (see Openshaw, et al. (1995) *J. Exp. Med.* 182:1357-1367; activated with anti-CD3 for 2, 6, 16 h pooled; T203); CD44− CD25+ pre T cells, sorted from thymus (T204); TH1 T cell clone D1.1, resting for 3 weeks after last stimulation with antigen (T205); TH1 T cell clone D1.1, 10 µg/ml ConA stimulated 15 h (T206); TH2 T cell clone CDC35, resting for 3 weeks after last stimulation with antigen (T207); TH2 T cell clone CDC35, 10 µg/ml ConA stimulated 15 h (T208); Mel14+ naive T cells from spleen, resting (T209); Mel14+ T cells, polarized to Th1 with IFN-γ/IL-12/anti-IL-4 for 6, 12, 24 h pooled (T210); Mel14+ T cells, polarized to Th2 with IL-4/anti-IFN-γ for 6, 13, 24 h pooled (T211); unstimulated mature B cell leukemia cell line A20 (B200); unstimulated B cell line CH12 (B201); unstimulated large B cells from spleen (B202); B cells from total spleen, LPS activated (B203); metrizamide enriched dendritic cells from spleen, resting (D200); dendritic cells from bone marrow, resting (D201); monocyte cell line RAW 264.7 activated with LPS 4 h (M200); bone-marrow macrophages derived with GM and M-CSF (M201); macrophage cell line J774, resting (M202); macrophage cell line J774+LPS+anti-IL-10 at 0.5, 1, 3, 6, 12 h pooled (M203); macrophage cell line J774+LPS+IL-10 at 0.5, 1, 3, 5, 12 h pooled (M204); aerosol challenged mouse lung tissue, Th2 primers, aerosol OVA challenge 7, 14, 23 h pooled (see Garlisi, et al. (1995) *Clinical Immunology and Immunopathology* 75:75-83; X206); Nippostrongulus-infected lung tissue (see Coffman, et al. (1989) *Science* 245:308-310; X200); total adult lung, normal (O200); total lung, rag-1 (see Schwarz, et al. (1993) *Immunodeficiency* 4:249-252; O205); IL-10 K.O. spleen (see Kuhn, et al. (1991) *Cell* 75:263-274; X201); total adult spleen, normal (O201); total spleen, rag-1 (O207); IL-10 K.O. Peyer's patches (O202); total Peyer's patches, normal (O210); IL-10 K.O. mesenteric lymph nodes (X203); total mesenteric lymph nodes, normal (O211); IL-10 K.O. colon (X203); total colon, normal (O212); NOD mouse pancreas (see Makino, et al. (1980) *Jikken Dobutsu* 29:1-13; X205); total thymus, rag-1 (O208); total kidney, rag-1 (O209); total heart, rag-1 (O202); total brain, rag-1 (O203); total testes, rag-1 (O204); total liver, rag-1 (O206); rat normal joint tissue (O300); and rat arthritic joint tissue (X300).

Samples for human mRNA isolation may include: peripheral blood mononuclear cells (monocytes, T cells, NK cells, granulocytes, B cells), resting (T100); peripheral blood mononuclear cells, activated with anti-CD3 for 2, 6, 12 h pooled (T101); T cell, TH0 clone Mot 72, resting (T102); T cell, TH0 clone Mot 72, activated with anti-CD28 and anti-CD3 for 3, 6, 12 h pooled (T103); T cell, TH0 clone Mot 72, anergic treated with specific peptide for 2, 7, 12 h pooled (T104); T cell, TH1 clone HY06, resting (T107); T cell, TH1 clone HY06, activated with anti-CD28 and anti-CD3 for 3, 6, 12 h pooled (T108); T cell, TH1 clone HY06, anergic treated with specific peptide for 2, 6, 12 h pooled (T109); T cell, TH2 clone HY935, resting (T110); T cell, TH2 clone HY935, activated with anti-CD28 and anti-CD3 for 2, 7, 12 h pooled (T111); T cells CD4+CD45RO− T cells polarized 27 days in anti-CD28, IL-4, and anti IFN-γ, TH2 polarized, activated with anti-CD3 and anti-CD28 4 h (T116); T cell tumor lines Jurkat and Hut78, resting (T117); T cell clones, pooled AD130.2, Tc783.12, Tc783.13, Tc783.58, Tc782.69, resting (T118); T cell random γδ T cell clones, resting (T119); Splenocytes, resting (B100); Splenocytes, activated with anti-CD40 and IL-4 (B101); B cell EBV lines pooled WT49, RSB, JY, CVIR, 721.221, RM3, HSY, resting (B102); B cell line JY, activated with PMA and ionomycin for 1, 6 h pooled (B103); NK 20 clones pooled, resting (K100); NK 20 clones pooled, activated with PMA and ionomycin for 6 h (K101); NKL clone, derived from peripheral blood of LGL leukemia patient, IL-2 treated (K106); NK cytotoxic clone 640-A30-1, resting (K107); hematopoietic precursor line TF1, activated with PMA and ionomycin for 1, 6 h pooled (C100); U937 premonocytic line, resting (M100); U937 premonocytic line, activated with PMA and ionomycin for 1, 6 h pooled (M101); elutriated monocytes, activated with LPS, IFNγ, anti-IL-10 for 1, 2, 6, 12, 24 h pooled (M102); elutriated monocytes, activated with LPS, IFNγ, IL-10 for 1, 2, 6, 12, 24 h pooled (M103); elutriated monocytes, activated with LPS, IFNγ, anti-IL-10 for 4, 16 h pooled (M106); elutriated monocytes, activated with LPS, IFNγ, IL-10 for 4, 16 h pooled (M107); elutriated monocytes, activated LPS for 1 h (M108); elutriated monocytes, activated LPS for 6 h (M109); DC 70% CD1a+, from CD34+ GM-CSF, TNFα12 days, resting (D101); DC 70% CD1a+, from CD34+ GM-CSF, TNFα 12 days, activated with PMA and ionomycin for 1 hr (D102); DC 70% CD1a+, from CD34+ GM-CSF, TNFα12 days, activated with PMA and ionomycin for 6 hr (D103); DC 95% CD1a+, from CD34+ GM-CSF, TNFα12 days FACS sorted, activated with PMA and ionomycin for 1, 6 h pooled (D104); DC 95% CD14+, ex CD34+ GM-CSF, TNFα 12 days FACS sorted, activated with PMA and ionomycin 1, 6 hr pooled (D105); DC CD1a+ CD86+, from CD34+ GM-CSF, TNFα12 days FACS sorted, activated with PMA and ionomycin for 1, 6 h pooled (D106); DC from monocytes GM-CSF, IL-4 5 days, resting (D107); DC from monocytes GM-CSF, IL-4 5 days, resting (D108); DC from monocytes GM-CSF, IL-4 5 days, activated LPS 4, 16 h pooled (D109); DC from monocytes GM-CSF, IL-4 5 days, activated TNFα, monocyte supe for 4, 16 h pooled (D110); leiomyoma L11 benign tumor (X101); normal myometrium M5 (O115); malignant leiomyosarcoma GS1 (X103); lung fibroblast sarcoma line MRC5, activated with PMA and ionomycin for 1, 6 h pooled (C101); kidney epithelial carcinoma cell line CHA, activated with PMA and ionomycin for 1, 6 h pooled (C102); kidney fetal 28 wk male (O100); lung fetal 28 wk male (O101); liver fetal 28 wk male (O102); heart fetal 28 wk male (O103); brain fetal 28 wk male (O104); gallbladder fetal 28 wk male (O106); small intestine fetal 28 wk male (O107); adipose tissue fetal 28 wk male (O108); ovary fetal 25 wk female (O109); uterus fetal 25 wk female (O110); testes fetal 28 wk male (O111); spleen fetal 28 wk male (O112); adult placenta 28 wk (O113); and tonsil inflamed, from 12 year old (X100).

With a cDNA Southern, the human DIRS1 was found in LPS activated dendritic cells ("DC LPS"); monokine activated dendritic cells ("DC mix"); normal skin; Psoriasis skin; inflamed tonsil; fetal liver; fetal small intestine; fetal ovary; resting "70% dendritic cells"; 6 hr activated 70% dendritic cells; and LPS activated monocytes. A signal was also detected in normal monkey lung and Ascaris-challenged monkey lung (24 h), which indicates cross species hybridization. The following libraries had weaker expression of DIRS1: smoker lung pool; fetal spleen CD4+ T cells (TH2 polarized); gamma delta T cells; activated splenocytes; and B cells.

HOFNy28 (DIRS2) is expressed in U937 (a premonocytic cell line) cells, both resting and activated; activated A549 cells (epithelial cells, IL-1β activated); fetal uterus; fetal testes; and fetal spleen. This data is from PCR on these cDNA libraries followed by Southern hybridization.

Similar samples may isolated in other species for evaluation.

V. Cloning of Species Counterparts of DIRS1 or DIRS2

Various strategies are used to obtain species counterparts of, e.g., the DIRS1, preferably from other primates or rodents. One method is by cross hybridization using closely related species DNA probes. It may be useful to go into evolutionarily similar species as intermediate steps. Another method is by using specific PCR primers based on the identification of blocks of similarity or difference between genes, e.g., areas of highly conserved or nonconserved polypeptide or nucleotide sequence. Database sequence searches may also identify species counterparts.

VI. Production of Mammalian DIRS1 or DIRS2 Protein

An appropriate, e.g., GST, fusion construct is engineered for expression, e.g., in *E. coli*. For example, a mouse IGIF pGex plasmid is constructed and transformed into *E. coli*. Freshly transformed cells are grown, e.g., in LB medium containing 50 μg/ml ampicillin and induced with IPTG (Sigma, St. Louis, Mo.). After overnight induction, the bacteria are harvested and the pellets containing the DIRS1 protein are isolated. The pellets are homogenized, e.g., in TE buffer (50 mM Tris-base pH 8.0, 10 mM EDTA and 2 mM pefabloc) in 2 liters. This material is passed through a microfluidizer (Microfluidics, Newton, Mass.) three times. The fluidized supernatant is spun down on a Sorvall GS-3 rotor for 1 h at 13,000 rpm. The resulting supernatant containing the cytokine receptor protein is filtered and passed over a glutathione-SEPHAROSE column equilibrated in 50 mM Tris-base pH 8.0. The fractions containing the DIRS1-GST fusion protein are pooled and cleaved, e.g., with thrombin (Enzyme Research Laboratories, Inc., South Bend, Ind.). The cleaved pool is then passed over a Q-SEPHAROSE column equilibrated in 50 mM Tris-base. Fractions containing DIRS1 are pooled and diluted in cold distilled $H_2O$, to lower the conductivity, and passed back over a fresh Q-Sepharose column, alone or in succession with an immunoaffinity antibody column. Fractions containing the DIRS1 protein are pooled, aliquoted, and stored in the −70° C. freezer.

Comparison of the CD spectrum with cytokine receptor protein may suggest that the protein is correctly folded. See Hazuda, et al. (1969) *J. Biol. Chem.* 264:1689-1693.

VII. Determining Physiological Forms of Receptors

The cellular forms of receptors for ligands can be tested with the various ligands and receptor subunits provided, e.g., IL-10 related sequences. In particular, multiple cytokine receptor like ligands have been identified, see, e.g., U.S. Pat. No. 5,989,867 issued to Knappe, et al., which are incorporated herein by reference.

Cotransformation of the DIRS1 with putative other receptor subunit genes may be performed. In particular, the DSRS1 is suggested to be a second receptor subunit needed for functional receptor signaling. Such cells may be used to screen putative cytokine ligands, such as the DIL-30, for signaling. A cell proliferation assay may be used.

In addition, it has been known that many cytokine receptors function as heterodimers. The IL-1α and IL-1β ligands bind an IL-1R1 as the primary receptor and this complex then forms a high affinity receptor complex with the IL-1R3. As indicated above, the sequence similarity to IL-12 receptor subunits suggests functional similarity of the functional receptor, e.g., a soluble alpha subunit, and transmembrane beta subunit.

These subunit combinations can be tested now with the provided reagents. In particular, appropriate constructs can be made for transformation or transfection of subunits into cells. Constructs for the alpha chains, e.g., DSRS1 forms, can be made. Likewise for the beta subunit DIRS1. Combinatorial transfections of transformations can make cells expressing defined subunits, which can be tested for response to the predicted ligands. Appropriate cell types can be used, e.g., 293 T cells, with, e.g., an NFκb reporter construct.

Biological assays will generally be directed to the ligand binding feature of the protein or to the kinase/phosphatase activity of the receptor. The activity will typically be reversible, as are many other enzyme reactions, and may mediate phosphatase or phosphorylase activities, which activities are easily measured by standard procedures. See, e.g., Hardie, et al. (eds. 1995) *The Protein Kinase FactBook* vols. I and II, Academic Press, San Diego, Calif.; Hanks, et al. (1991) *Meth. Enzymol.* 200:38-62; Hunter, et al. (1992) *Cell* 70:375-388; Lewin (1990) *Cell* 61:743-752; Pines, et al. (1991) *Cold Spring Harbor Symp. Quant. Biol.* 56:449-463; and Parker, et al. (1993) *Nature* 363:736-738.

The family of cytokines contains molecules which are important mediators of hematopoiesis or inflammatory disease. See, e.g., Thomson (ed. 1994) *The Cytokine Handbook* Academic Press, San Diego; and Dinarello (1996) *Blood* 87:2095-2147.

VIII. Antibodies Specific for DIRS1 or DIRS2

Inbred Balb/c mice are immunized intraperitoneally with recombinant forms of the protein, e.g., purified DIRS1 or stable transfected NIH-3T3 cells. Animals are boosted at appropriate time points with protein, with or without additional adjuvant, to further stimulate antibody production. Serum is collected, or hybridomas produced with harvested spleens.

Alternatively, Balb/c mice are immunized with cells transformed with the gene or fragments thereof, either endogenous or exogenous cells, or with isolated membranes enriched for expression of the antigen. Serum is collected at the appropriate time, typically after numerous further administrations. Various gene therapy techniques may be useful, e.g., in producing protein in situ, for generating an immune response. Serum may be immunoselected or depleted to prepare substantially purified antibodies of defined specificity and high affinity. Preparations which specifically bind particular segments or defined epitopes may be made.

Monoclonal antibodies may be made. For example, splenocytes are fused with an appropriate fusion partner and hybridomas are selected in growth medium by standard procedures. Hybridoma supernatants are screened for the presence of antibodies which bind to the DIRS1, e.g., by ELISA or other assay. Antibodies which specifically recognize specific DIRS1 embodiments may also be selected or prepared.

In another method, synthetic peptides or purified protein are presented to an immune system to generate monoclonal or polyclonal antibodies. See, e.g., Coligan (ed. 1991) *Current Protocols in Immunology* Wiley/Greene; and Harlow and Lane (1989) *Antibodies: A Laboratory Manual* Cold Spring Harbor Press. In appropriate situations, the binding reagent is either labeled as described above, e.g., fluorescence or otherwise, or immobilized to a substrate for panning methods. Nucleic acids may also be introduced into cells in an animal to produce the antigen, which serves to elicit an immune response. See, e.g., Wang, et al. (1993) *Proc. Nat'l. Acad. Sci.* 90:4156-4160; Barry, et al. (1994) *BioTechniques* 16:616-619; and Xiang, et al. (1995) *Immunity* 2: 129-135.

Moreover, antibodies which may be useful to determine the combination of the DIRS1 with a functional alpha subunit may be generated. Thus, e.g., epitopes characteristic of a particular functional alpha/beta combination may be identified with appropriate antibodies.

IX. Production of Fusion Proteins with DIRS1 or DIRS2

Various fusion constructs are made with DIRS1 or DIRS2. A portion of the appropriate gene is fused to an epitope tag, e.g., a FLAG tag, or to a two hybrid system construct. See, e.g., Fields and Song (1989) *Nature* 340:245-246.

The epitope tag may be used in an expression cloning procedure with detection with anti-FLAG antibodies to detect a binding partner, e.g., ligand for the respective cytokine receptor. The two hybrid system may also be used to isolate proteins which specifically bind to DIRS1.

X. Structure Activity Relationship

Information on the criticality of particular residues is determined using standard procedures and analysis. Standard mutagenesis analysis is performed, e.g., by generating many different variants at determined positions, e.g., at the positions identified above, and evaluating biological activities of the variants. This may be performed to the extent of determining positions which modify activity, or to focus on specific positions to determine the residues which can be substituted to either retain, block, or modulate biological activity.

Alternatively, analysis of natural variants can indicate what positions tolerate natural mutations. This may result from populational analysis of variation among individuals, or across strains or species. Samples from selected individuals are analyzed, e.g., by PCR analysis and sequencing. This allows evaluation of population polymorphisms.

XI. Isolation of a Ligand for DIRS1 or DIRS2

A cytokine receptor can be used as a specific binding reagent to identify its binding partner, by taking advantage of its specificity of binding, much like an antibody would be used. Typically, the binding receptor is a heterodimer of receptor subunits. A binding reagent is either labeled as described above, e.g., fluorescence or otherwise, or immobilized to a substrate for panning methods.

The binding composition is used to screen an expression library made from a cell line which expresses a binding partner, i.e., ligand, preferably membrane associated. Standard staining techniques are used to detect or sort surface expressed ligand, or surface expressing transformed cells are screened by panning. Screening of intracellular expression is performed by various staining or immunofluorescence procedures. See also McMahan, et al. (1991) *EMBO J.* 10:2821-2832.

For example, on day 0, precoat 2-chamber permanox slides with 1 ml per chamber of fibronectin, 10 ng/ml in PBS, for 30 min at room temperature. Rinse once with PBS. Then plate COS cells at $2-3 \times 10^5$ cells per chamber in 1.5 ml of growth media. Incubate overnight at 37° C.

On day 1 for each sample, prepare 0.5 ml of a solution of 66 μg/ml DEAE-dextran, 66 μM chloroquine, and 4 μg DNA in serum free DME. For each set, a positive control is prepared, e.g., of DIRS1—FLAG cDNA at 1 and 1/200 dilution, and a negative mock. Rinse cells with serum free DME. Add the DNA solution and incubate 5 hr at 37° C. Remove the medium and add 0.5 ml 10% DMSO in DME for 2.5 min.

Remove and wash once with DME. Add 1.5 ml growth medium and incubate overnight.

On day 2, change the medium. On days 3 or 4, the cells are fixed and stained. Rinse the cells twice with Hank's Buffered Saline Solution (HBSS) and fix in 4% paraformaldehyde (PFA)/glucose for 5 min. Wash 3× with HBSS. The slides may be stored at −80° C. after all liquid is removed. For each chamber, 0.5 ml incubations are performed as follows. Add HBSS/saponin (0.1%) with 32 µl/ml of 1 M NaN$_3$ for 20 min. Cells are then washed with HBSS/saponin 1×. Add appropriate DIRS1 or DIRS1/antibody complex to cells and incubate for 30 min. Wash cells twice with HBSS/saponin. If appropriate, add first antibody for 30 min. Add second antibody, e.g., Vector anti-mouse antibody, at 1/200 dilution, and incubate for 30 min. Prepare ELISA solution, e.g., Vector Elite ABC horseradish peroxidase solution, and preincubate for 30 min. Use, e.g., 1 drop of solution A (avidin) and 1 drop solution B (biotin) per 2.5 ml HBSS/saponin. Wash cells twice with HBSS/saponin. Add ABC HRP solution and incubate for 30 min. Wash cells twice with HBSS, second wash for 2 min, which closes cells. Then add Vector diaminobenzoic acid (DAB) for 5 to 10 min. Use 2 drops of buffer plus 4 drops DAB plus 2 drops of H$_2$O$_2$ per 5 ml of glass distilled water. Carefully remove chamber and rinse slide in water. Air dry for a few minutes, then add 1 drop of Crystal Mount and a cover slip. Bake for 5 min at 85-90° C.

Evaluate positive staining of pools and progressively subclone to isolation of single genes responsible for the binding.

Alternatively, receptor reagents are used to affinity purify or sort out cells expressing a putative ligand. See, e.g., Sambrook, et al. or Ausubel, et al.

Another strategy is to screen for a membrane bound receptor by panning. The receptor cDNA is constructed as described above. The ligand can be immobilized and used to immobilize expressing cells. Immobilization may be achieved by use of appropriate antibodies which recognize, e.g., a FLAG sequence of a DIRS1 fusion construct, or by use of antibodies raised against the first antibodies. Recursive cycles of selection and amplification lead to enrichment of appropriate clones and eventual isolation of receptor expressing clones.

Phage expression libraries can be screened by mammalian DIRS1. Appropriate label techniques, e.g., anti-FLAG antibodies, will allow specific labeling of appropriate clones.

All citations herein are incorporated herein by reference to the same extent as if each individual publication or patent application was specifically and individually indicated to be incorporated by reference.

Many modifications and variations of this invention can be made without departing from its spirit and scope, as will be apparent to those skilled in the art. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

What is claimed is:

1. An isolated polypeptide comprising the amino acid sequence of SEQ ID NO: 2.

2. The polypeptide of claim 1, which is produced by a recombinant host cell.

3. The polypeptide of claim 1, which comprises a heterologous protein.

4. The polypeptide of claim 3, wherein the heterologous protein is selected from the group consisting of a FLAG-tag, a His-6 tag, an Ig, luciferase, glutathione-S-transferase (GST), bacterial β-galactosidase, trpE, β-lactamase, alpha amylase, alcohol dehydrogenase, and yeast alpha mating factor.

5. The polypeptide of claim 1, which is glycosylated.

6. An isolated polypeptide comprising amino acids 30-311 of SEQ ID NO: 2.

7. The polypeptide of claim 6, which is produced by a recombinant host cell.

8. The polypeptide of claim 6, which comprises a heterologous protein.

9. The polypeptide of claim 8, wherein the heterologous protein is selected from the group consisting of a FLAG-tag, a His-6 tag, an Ig, luciferase, glutathione-S-transferase (GST), bacterial β-galactosidase, trpE, β-lactamase, alpha amylase, alcohol dehydrogenase, and yeast alpha mating factor.

10. The polypeptide of claim 6, which is glycosylated.

\* \* \* \* \*